(12) United States Patent
Takakura et al.

(10) Patent No.: US 9,611,303 B2
(45) Date of Patent: *Apr. 4, 2017

(54) MODIFIED BIOTIN-BINDING PROTEIN

(71) Applicant: Japan Tobacco Inc., Tokyo (JP)

(72) Inventors: Yoshimitsu Takakura, Iwata (JP); Masako Tsunashima, Iwata (JP); Kozue Sofuku, Iwata (JP)

(73) Assignee: JAPAN TOBACCO INC., Tokyo (JP)

( * ) Notice: Subject to any disclaimer, the term of this patent is extended or adjusted under 35 U.S.C. 154(b) by 61 days.

This patent is subject to a terminal disclaimer.

(21) Appl. No.: 14/661,672

(22) Filed: Mar. 18, 2015

(65) Prior Publication Data

US 2015/0291671 A1    Oct. 15, 2015

Related U.S. Application Data

(63) Continuation of application No. 13/378,282, filed as application No. PCT/JP2009/061530 on Jun. 24, 2009, now Pat. No. 9,018,360.

(51) Int. Cl.
*C07K 14/00* (2006.01)
*C07K 17/00* (2006.01)
*C07K 14/375* (2006.01)

(52) U.S. Cl.
CPC ........ *C07K 14/375* (2013.01); *C07K 2319/22* (2013.01); *G01N 2333/36* (2013.01)

(58) Field of Classification Search
None
See application file for complete search history.

(56) References Cited

U.S. PATENT DOCUMENTS

| 6,312,916 | B1 | 11/2001 | Kopetzki et al. | |
|---|---|---|---|---|
| 8,343,727 | B2 | 1/2013 | Takakura et al. | |
| 9,018,360 | B2 * | 4/2015 | Takakura | C07K 14/375 424/184.1 |
| 2005/0089983 | A1 * | 4/2005 | Takakura | A01N 63/04 435/200 |
| 2010/0176179 | A1 | 7/2010 | Aoki | |
| 2010/0311076 | A1 | 12/2010 | Takakura et al. | |
| 2010/0330701 | A1 | 12/2010 | Takakura et al. | |
| 2011/0284408 | A1 | 11/2011 | Aoki | |

FOREIGN PATENT DOCUMENTS

| EP | 0 799 890 A2 | 10/1997 |
|---|---|---|
| EP | 2 112 168 A1 | 10/2009 |
| EP | 2 184 356 A1 | 5/2010 |
| EP | 2314681 A1 | 4/2011 |
| JP | 10-28589 | 2/1998 |
| WO | 01/05977 A1 | 1/2001 |
| WO | 02/072817 A1 | 9/2002 |
| WO | WO 2004/018509 A1 | 3/2004 |
| WO | WO 2008/018509 A1 | 2/2008 |
| WO | WO 2008/081938 A1 | 7/2008 |
| WO | WO 2009/028625 A1 | 3/2009 |

OTHER PUBLICATIONS

Chilkoti et al., "Site-directed mutagenesis studies of the high-affinity streptavidin-biotin complex: Contributions of tryptophan residues 79, 108, and 120," Proceedings of the National Academy of Sciences of the United States of America, vol. 92, Feb. 1995, pp. 1754-1758.
Extended European Search Report, dated Nov. 19, 2012, for European Application No. 09846508.1.
Greenspan et al. 1999 (Defining epitopes: It's not as easy as it seems; Nature Biotechnology, 17:936-937).
Guo et al. ("Protein tolerance to random amino acid change", Proceedings of the National Academy of Science USA, vol. 101, No. 5, pp. 9205-9210, 2004).
International Search Report dated Aug. 25, 2009 for International Application No. PCT/JP2009/061530.
Laitinen et al., "Biotin Induces Tetramerization of a Recombinant Monomeric Avidin," The Journal of Biological Chemistry, vol. 276, No. 11, Mar. 16, 2001, pp. 8219-8224.
Laitinen et al., "Genetically engineered avidins and streptavidins," Cellular and Molecular Life Sciences, vol. 63, 2006, pp. 2992-3017.
Laitinen et al., "Mutation of a critical tryptophan to lysine in avidin or streptavidin may explain why sea urchin fibropellin adopts an avidin-like domain," FEBS Letters, vol. 461, 1999, pp. 52-58.
Laitinen et al., "Rational Design of an Active Avidin Monomer," The Journal of Biological Chemistry, vol. 278, No. 6, Feb. 7, 2003, pp. 4010-4014.

(Continued)

*Primary Examiner* — Gary Nickol
*Assistant Examiner* — Mary Lyons
(74) *Attorney, Agent, or Firm* — Birch, Stewart, Kolasch & Birch, LLP

(57) ABSTRACT

The present invention provides a modified biotin-binding protein comprising an amino acid sequence represented by SEQ ID NO: 2 or its modified sequence and having a biotin-binding activity and replacement selected from the group consisting of:
1) replacement of the 36th serine residue of SEQ ID NO: 2 with an amino acid residue that does not form a hydrogen bond;
2) replacement of the 80th tryptophan residue of SEQ ID NO: 2 with a hydrophilic amino acid residue;
3) replacement of the 116th aspartic acid residue of SEQ ID NO: 2 with an amino acid residue that does not form a hydrogen bond;
4) replacement of the 46th proline residue of SEQ ID NO: 2 with a threonine, serine, or tyrosine residue and replacement of the 78th threonine residue of SEQ ID NO: 2 with an amino acid residue that does not form a hydrogen bond;
5) replacement of the 46th proline residue of SEQ ID NO: 2 with a threonine, serine, or tyrosine residue and replacement of the 116th aspartic acid residue of SEQ ID NO: 2 with an amino acid that does not form a hydrogen bond; and
6) replacement of the 46th proline residue of SEQ ID NO: 2 with a threonine, serine, or tyrosine residue, replacement of the 78th threonine residue of SEQ ID NO: 2 with an amino acid residue that does not form a hydrogen bond, and replacement of the 116th aspartic acid residue of SEQ ID NO: 2 with an amino acid that does not form a hydrogen bond.

12 Claims, 8 Drawing Sheets

(56) References Cited

OTHER PUBLICATIONS

Marttila et al., "Mutation of the important Tyr-33 residue of chicken avidin: functional and structural consequences," Biochemical Journal, vol. 369, 2003, pp. 249-254.

Qureshi et al., "Design, production, and characterization of a monomeric streptavidin and its application for affinity purification of biotinylated proteins," Protein Expression and Purification, vol. 25, 2002, pp. 409-415.

Qureshi et al., "Development and Characterization of a Series of Soluble Tetrameric and Monomeric Streptavidin Muteins with Differential Biotin Binding Affinities," The Journal of Biological Chemistry, vol. 276, No. 49, Dec. 7, 2001, pp. 46422-46428.

Reznik et al., "A streptavidin mutant with altered ligand-binding specificity," Proceedings of the National Academy of Sciences of the United States of America, vol. 95, Nov. 1998, pp. 13525-13530.

Sano et al., "Engineering subunit association of multisubunit proteins: A dimeric streptavidin," Proceedings of the National Academy of Sciences of the United States of America, vol. 94, Jun. 1997, pp. 6153-6158.

Sano et al., "Intersubunit contacts made by tryptophan 120 with biotin are essential for both strong biotin binding and biotin-induced tighter subunit association of streptavidin," Proceedings of the National Academy of Sciences of the United States of America, vol. 92, Apr. 1995, pp. 3180-3184.

Supplementary European Search Report for European Application No. 09846508.1, dated Jan. 30, 2013.

Takakura et al., "Tamavidins—novel avidin-like biotin-binding proteins from the Tamogitake mushroom," FEBS Journal, vol. 276, No. 5, 2009, pp. 1383-1397.

Wu et al., "Engineering Soluble Monomeric Stretavidin with Reversible Biotin Binding Capability," The Journal of Biological Chemistry, vol. 280, No. 24, Jun. 17, 2005, pp. 23225-23231.

Wu et al., "Intracellular production of a soluble and functional monomeric streptavidin in *Escherichia coli* and its application for affinity purification of biotinylated proteins," Protein Expression and Purification, vol. 46, 2006, pp. 268-273.

\* cited by examiner

MODIFIED BIOTIN-BINDING PROTEIN

This application is a Continuation of copending application Ser. No. 13/378,282, filed on Dec. 14, 2011, which was filed as PCT International Application No. PCT/JP2009/061530 on Jun. 24, 2009, all of which are hereby expressly incorporated by reference into the present application.

TECHNICAL FIELD

The present invention relates to a modified biotin-binding protein.

BACKGROUND ART

Avidin is a basic glycoprotein derived from albumen and strongly binds to biotin (vitamin H). On the other hand, streptavidin is an avidin-like protein derived from *Streptomyces avidinii* and has an approximately neutral isoelectric point and does not have a sugar chain. Both proteins form tetramers, and one subunit binds to one biotin molecule. The molecular weights are about 60 kDa. The affinity of avidin to biotin or of streptavidin to biotin is very high ($Kd=10^{-15}$ to $10^{-14}$ M) and is the highest as interaction between two biomolecules. Accordingly, avidin/streptavidin-biotin interaction has been widely used in the fields of biochemistry, molecular biology, and medicine. Avidin has an isoelectric point higher than 10, and this high basicity or the presence of a sugar chain problematically causes non-specific binding to biomolecules, such as DNA and protein, in some cases.

Biotin has a small molecular weight of 244 and is stable for a change in pH and heat and, therefore, is commonly used as a label of substances. In a method of biotinylation, chemically modified biotin is bound to a functional group of protein, such as an amino group, a carboxyl group, or an aldehyde group. Biotinylating reagents are commercially available and can be used to biotinylate protein, nucleic acid, and other substances. In a method of biotinylating protein, a fusion protein of a target protein and a sequence that will be biotinylated by biotin ligase in vivo is expressed as a recombinant protein, and the resulting fusion protein is biotinylated by the biotin ligase in a host cell. For example, BIOEASE TAG™ (biotinylated sequence) is a biotinylated sequence supplied by Life Technologies Corporation and is on the market as a system for expressing a biotinylated protein in vivo, in *E. coli, drosophila*, or mammal cells.

The binding between avidin or streptavidin and biotin is significantly strong and is thus irreversible, and the both are hardly dissociated from each other after the binding is formed once. Because of this strong binding, known avidin and streptavidin cannot be directly applied to technical fields that require reversible binding, such as affinity chromatography, for purifying biotinylated biomolecules.

Countermeasures which have been reported against this problem are avidin and streptavidin showing reduced biotin-binding affinity. For example, nitrated avidin and nitrated streptavidin in which the tyrosine residue contributing to binding to biotin is nitrated have been developed. They strongly bind to biotin under acidic to neutral conditions (pH 4 to 7.5) and are dissociated from biotin under alkaline conditions (pH 10). Nitrated avidin agarose is commercially available as CAPTAVIDIN-AGAROSE™ (nitrated avidin agarose). However, nitration is a troublesome task, and its efficiency is not constant. In addition, an extreme change in pH may adversely affect biotinylated protein and so on.

At the same time, it has been reported to reduce the affinity to biotin by introducing site-specific amino acid mutation to avidin or streptavidin through genetic engineering. Two methods are known for reducing affinity to biotin: a method of introducing a modification into an amino acid that directly interacts with biotin among amino acids forming a biotin-binding pocket; and a method of introducing a modification into an amino acid that is involved in the interaction between subunits of the protein.

In the case of avidin, recombinant proteins having reduced affinity to biotin have been reported in which a modification is introduced to the amino acid that forms a hydrogen bond with biotin (Marttila, et al., (2003), Biochem. J., 369: 249-254; Laitinen, et al., (2003), J. Biol. Chem., 278: 4010-4014; Laitinen, et al., (2001), J. Biol. Chem., 276: 8219-8224) or a modification is introduced to the amino acid that forms a hydrophobic bond with biotin (Laitinen, et al., (1999) FEBS Lett., 461: 52-58; Laitinen, et al., (2003), J. Biol. Chem., 278: 4010-4014).

Similarly, in the case of streptavidin, examples are known in which a modification is introduced to the amino acid that forms a hydrogen bond with biotin (Qureshi, et al., (2001), J. Biol. Chem., 276: 46422-46428; Gabriel, et al., (1998), Proc. Natl. Acad. Sci., 95: 13525-13530; Qureshi and Wong, (2002), Protein Expr. Purif., 25: 409-415; Wu and Wong, (2006), Protein Expr. Purif., 46: 268-273; Wu and Wong, (2005), J. Biol. Chem., 280: 23225-23231) or a modification is introduced to the amino acid that forms a hydrophobic bond with biotin (Chilkoti, et al., (1995), Proc. Natl. Acad. Sci., 92: 1754-1758; Laitinen, et al., (1999), FEBS Lett., 461: 52-58; Sano, et al., (1995), Proc. Natl. Acad. Sci., 92: 3180-3184; Sano, et al., (1997), Proc. Natl. Acad. Sci., 94: 6153-6158).

Furthermore, in the cases of avidin and streptavidin, it has been reported to produce monomers of these proteins that are modified to reduce the affinity to biotin by introducing the modification to the amino acids involving in the interaction between subunits of these proteins (Laitinen, et al., (2001), J. Biol. Chem., 276: 8219-8224; Wu and Wong, (2005), J. Biol. Chem., 280: 23225-23231). Avidin and streptavidin each form a tetramer, and each subunit has one biotin-binding site. In order to form a complete biotin-binding pocket, the amino acid residue present in the adjacent subunit (for example, in the case of tamavidin 2, the 108th tryptophan (W108)) is important. Accordingly, it is believed that the binding between subunits also highly affect the affinity to biotin.

According to Wu, et al, (J. Biol. Chem., (2005), 280: 23225-23231), in the case of subunits of streptavidin designated as A, B, C, and D, the 55th valine of subunit A is present near the 59th arginine of subunit B. The 76th threonine of subunit A is present very close to the 76th threonine and the 59th alanine of subunit B. The 109th leucine of subunit B interacts with the 125th valine of subunit A. The 125th valine of subunit A widely interacts with the 109th leucine, the 120th tryptophan, the 123rd threonine, and 125th valine of subunit D, the 109th leucine of subunit B, and 107th glutamine of subunit C. Accordingly, charge repulsion or steric hindrance between subunits are expected to be generated through replacing these amino acids with highly polar amino acids such as arginine, lysine, histidine, aspartic acid, glutamic acid, asparagine, glutamine, and threonine. It is conceivable that arginine having the lowest hydrophaty index among these polar amino acids is particularly effective.

In order to apply the biotin-binding protein such as avidin and streptavidin to the technical field that requires reversible binding, such as affinity chromatography, a possible goal is to increase the dissociation constant (KD) to about $10^{-7}$ (M).

Though depending on circumstance, in general, a dissociation constant less than this level leads to high biotin-binding ability that precludes efficient dissociation of a desired biotinylated substance, while a dissociation constant higher than this level leads to low biotin-binding ability that precludes sufficient binding of a desired biotinylated substance (Wu and Wong, (2006), Protein Expr. Purif., 46: 268-27).

In light of these points, among the streptavidin mutants, every single-amino acid mutant at the hydrogen bond site has a low dissociation constant of about $10^{-11}$ (M) and significantly high biotin-binding ability. However, many of these mutants have an effect on the interaction between subunits by amino acid modification to often give monomers. In the case of the monomers, the dissociation constant is about $10^{-9}$ (M). Furthermore, among the streptavidin mutants, if two or more hydrogen bond sites are further modified, the tetramers are mostly dissociated into monomers, some of these monomers have a biotin-binding ability (dissociation constant) of about $10^{-8}$ to $10^{-6}$ (M) (Qureshi, et al., (2001), J. Biol. Chem., 276: 46422-46428).

Mutants having a dissociation constant of $10^{-8}$ to $10^{-7}$ (M) have biotin-binding ability suitable for application to, for example, affinity chromatography (Qureshi and Wong, (2002), Protein Expr. Purif., 25: 409-415; Wu and Wong, (2006), Protein Expr. Purif., 46: 268-273). However, these monomers are known to be easily decomposed by proteases (Laitinen, et al., (2001), J. Biol. Chem., 276: 8219-8224; Wu and Wong, (2005), J. Biol. Chem., 280: 23225-23231). Affinity chromatography often uses a crude cell extract containing various substances. Many of such crude cell extracts contain proteases to cause a problem when the monomers are used in such application.

In addition, in the monomers, the hydrophobic region that is hidden by the binding between subunits is exposed, which probably reduces the overall solubility of the protein and may cause reaggregation. In monomers designed using avidin as a model (for example, SOFTLINK™ Soft Release Avidin Resin (resin to which monomeric avidin as a model is immobilized), available from Promega Corp.), the monomers associate with one another to form a tetramer when they are immobilized to a carrier. As a result, the affinity with biotin is increased. Accordingly, it is necessary to fill the region of the tetramer that strongly binds to biotin with biotin before addition of as biotin-labeled substance. This treatment is a troublesome task and may highly affect the yield of the biotin-labeled substance depending on the degree of the pretreatment.

In a very small number of streptavidin mutants, the tetramer form is maintained even if amino acids at two positions of a hydrogen bond site are modified. However, in such a tetramer, the interaction between subunits is weakened due to the modification, and a phenomenon in which many of the monomers constituting the tetramer are dissolved is observed after a biotinylated substance bound to the tetramer immobilized to a carrier is eluted by adding an excess amount of biotin thereto.

Furthermore, many amino acid-modified proteins of avidin and streptavidin cannot be solubly expressed in E. coli and have to be expressed in insect cells or Bacillus subtilis cells (Laitinen, et al., (1999), FEBS Lett., 461: 52-58; Qureshi and Wong, (2002), Protein Expr. Purif., 25: 409-415), which raises labor and cost issues. Only some monomeric streptavidins can be solubly expressed in E. coli (Wu and Wong, (2006), Protein Expr. Purif., 46: 268-273).

As described above, it has not yet been known as biotin-binding protein that has biotin-binding ability allowing the protein to sufficiently bind to and to be dissociated from a desired biotinylated substance, that can be solubly expressed in E. coli, and that has protease resistance.

The present inventors have discovered tamavidin 1 and tamavidin 2, which are novel avidin-like biotin-binding proteins, in an edible mushroom (Pueurotus conucopiae) (WO02/072817). Tamavidin 1 and tamavidin 2 can be expressed in E. coli. In particular, tamavidin 2 can be easily prepared by purification using an iminobiotin column (WO02/072817). Tamavidin 1 and tamavidin 2 extremely strongly bind to biotin. In particular, tamavidin 2 shows a biotin-binding activity almost equal to that of avidin or streptavidin. Furthermore, tamavidin 2 is a biotin-binding protein excellent in that the heat resistance is higher than that of avidin or streptavidin and that the non-specific binding is less than that of avidin.

CITATION LIST

Patent Literature

Patent Literature 1: International Patent Publication No. WO02/072817

Non-Patent Literature

Non-Patent Literature 1: Marttila, et al., (2003), Biochem. J., 369: 249-254
Non-Patent Literature 2: Laitinen, et al., (2003), J. Biol. Chem., 278: 4010-4014
Non-Patent Literature 3: Laitinen, et al., (2001), J. Biol. Chem., 276: 8219-8224
Non-Patent Literature 4: Laitinen, et al., (1999), FEBS Lett., 461: 51-58
Non-Patent Literature 5: Qureshi, et al., (2001), J. Biol. Chem., 276: 46422-46428
Non-Patent Literature 6: Gabriel, et al., (1998), Proc. Natl. Acad. Sci., 95: 13525-13530
Non-Patent Literature 7: Qureshi and Wong, (2002), Protein Expr. Purif., 25: 409-415
Non-Patent Literature 8: Wu and Wong, (2006), Protein Expr. Purif., 46: 268-273
Non-Patent Literature 9: Wu and Wong, (2005), J. Biol. Chem., 280: 21225-21231
Non-Patent Literature 10: Chilkoti, et al., (1995), Proc. Natl. Acad. Sci., 92: 1754-1758
Non-Patent Literature 11: Sano, et al., (1995), Proc. Natl. Acad. Sci. 92: 3180-3184
Non-Patent Literature 12: Sano, et al., (1997), Proc. Natl. Acad. Sci., 94: 6153-6158

SUMMARY OF INVENTION

Technical Problem

It is an object of the present invention to provide a biotin-binding protein that can be solubly expressed at a high level in E. coli and can be readily purified with a biotin-immobilized carrier.

Solution to Problem

The present inventors have diligently studied in order to solve the foregoing problems and, as a result, have successfully obtained a stable modified biotin-binding protein having a biotin-binding ability that allows a desired biotinylated substance to sufficiently bind to and to be dissociated from the biotin-binding protein and having protease resistance, and have arrived at the present invention.

Specifically, in the present invention, a modified biotin-binding protein having the above-mentioned properties is obtained by modifying the amino acid sequence (SEQ ID NO:2) of natural tamavidin 2 (hereinafter may be referred to as "TM2" in this specification).

The present invention includes the following preferred embodiments.

Embodiment 1

A modified biotin-binding protein comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having a biotin-binding activity, the modified biotin-binding protein having replacement selected from the group consisting of:
  1) replacement of the 36th serine residue of SEQ ID NO: 2 with an amino acid residue that does not form a hydrogen bond;
  2) replacement of the 80th tryptophan residue of SEQ ID NO: 2 with a hydrophilic amino acid residue;
  3) replacement of the 116th aspartic acid residue of SEQ ID NO: 2 with an amino acid residue that does not form a hydrogen bond;
  4) replacement of the 46th proline residue of SEQ ID NO: 2 with a threonine, serine, or tyrosine residue and replacement of the 78th threonine residue of SEQ ID NO: 2 with an amino acid residue that does not form a hydrogen bond;
  5) replacement of the 46th proline residue of SEQ ID NO: 2 with a threonine, serine, or tyrosine residue and replacement of the 116th aspartic acid residue of SEQ ID NO: 2 with an amino acid that does not form a hydrogen bond; and
  6) replacement of the 46th proline residue of SEQ ID NO: 2 with a threonine, serine, or tyrosine residue, replacement of the 78th threonine residue of SEQ ID NO: 2 with an amino acid residue that does not form a hydrogen bond, and replacement of the 116th aspartic acid residue of SEQ ID NO: 2 with an amino acid that does not form a hydrogen bond.

Embodiment 2

The modified biotin-binding protein according to Embodiment 1, selected from the group consisting of:
  1-a) a modified biotin-binding protein (TM2 S36A) in which the 36th serine residue of SEQ ID NO: 2 is replaced with alanine;
  2-a) a modified biotin-binding protein (TM2 W80K) in which the 80th tryptophan residue of SEQ ID NO: 2 is replaced with lysine;
  3-a) a modified biotin-binding protein (TM2 D116A) in which the 116th aspartic acid residue of SEQ ID NO: 2 is replaced with alanine;
  4-a) a modified biotin-binding protein (TM2P46T-T78A) in which the 46th proline residue of SEQ ID NO: 2 is replaced with threonine and the 78th threonine residue of SEQ ID NO: 2 is replaced with alanine;
  5-a) a modified biotin-binding protein (TM2P46T-D116A) in which the 46th proline residue of SEQ ID NO: 2 is replaced with threonine and the 116th aspartic acid residue of SEQ ID NO: 2 is replaced with alanine; and
  6-a) a modified biotin-binding protein (TM2P46T-T78A-D116A) in which the 46th proline residue of SEQ ID NO: 2 is replaced with threonine, the 78th threonine residue of SEQ ID NO: 2 is replaced with alanine, and the 116th aspartic acid residue of SEQ ID NO: 2 is replaced with alanine.

Embodiment 3

The modified biotin-binding protein according to Embodiment 1 or 2, satisfying at least one of the following properties:
  i) allowing purification using biotin;
  ii) maintaining a tetramer structure of a protein comprising the amino acid sequence represented by SEQ ID NO: 2;
  iii) having protease resistance; and
  iv) showing high expression in a soluble fraction of $E.\ coli$.

Embodiment 4

A modified biotin-binding protein comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having a biotin-binding activity, the modified biotin-binding protein comprising:
  6) replacement of the 78th threonine residue of SEQ ID NO: 2 with an amino acid residue that does not form a hydrogen bond.

Embodiment 5

The modified biotin-binding protein according to Embodiment 4, wherein
  6-a) the 78th threonine residue of SEQ ID NO: 2 is replaced with alanine residue (TM2 T78A).

Embodiment 6

The modified biotin-binding protein according to Embodiment 4 or 5, satisfying at least one of the following properties:
  i) allowing purification using biotin;
  ii) maintaining a tetramer structure of a protein comprising the amino acid sequence represented by SEQ ID NO: 2;
  iii) having protease resistance; and
  v) having heat resistance higher than that of a protein comprising the amino acid sequence represented by SEQ ID NO: 2.

Embodiment 7

A modified biotin-binding protein comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having a biotin-binding activity, the modified biotin-binding protein having replacement selected from the group consisting of:
  7) replacement of the 36th serine residue of SEQ ID NO: 2 with an amino acid residue that does not form a hydrogen bond and replacement of the 116th aspartic acid residue of SEQ ID NO: 2 with an amino acid that does not form a hydrogen bond; and 8) replacement of the 36th serine residue of SEQ ID NO: 2 with an amino acid residue that does not form a hydrogen bond, replacement of the 78th threonine residue of SEQ ID NO: 2 with an amino acid residue that does not form a hydrogen bond, and replacement of the 116th aspartic acid residue of SEQ ID NO: 2 with an amino acid that does not form a hydrogen bond.

Embodiment 8

The biotin-binding protein according to Embodiment 7, selected from the group consisting of:

7-a) a modified biotin-binding protein (TM2 S36A-D116A) in which the 36th serine residue of SEQ ID NO: 2 is replaced with alanine, and the 116th aspartic acid residue of SEQ ID NO: 2 is replaced with alanine; and 8-a) a modified biotin-binding protein (TM2 S36A-T78A-D116A) in which the 36th serine residue of SEQ ID NO: 2 is replaced with alanine, the 78th threonine residue of SEQ ID NO: 2 is replaced with alanine, and the 116th aspartic acid residue of SEQ ID NO: 2 is replaced with alanine.

Embodiment 9

The modified biotin-binding protein according to Embodiment 7 or 8, satisfying at least one of the following properties:

i) allowing purification using biotin;
iii) having protease resistance; and
vi) binding to biotin under weak acidic conditions and not binding to biotin under neutral conditions.

Embodiment 10

A modified biotin-binding protein comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having a biotin-binding activity, the modified biotin-binding protein comprising 9) replacement of the 78th threonine residue of SEQ ID NO: 2 with an amino acid residue that does not form a hydrogen bond and replacement of the 116th aspartic acid residue of SEQ ID NO: 2 with an amino acid that does not form a hydrogen bond.

Embodiment 11

The modified biotin-binding protein according to Embodiment 10, wherein 9-a) the 78th threonine residue of SEQ ID NO: 2 is replaced with alanine, and the 116th aspartic acid residue of SEQ ED NO: 2 is replaced with alanine (TM2 T78A-D116A).

Embodiment 12

The modified biotin-binding protein according to Embodiment 10 or 11, satisfying at least one of the following properties:

i) allowing purification using biotin;
ii) maintaining a tetramer structure of a protein comprising the amino acid sequence represented by SEQ ID NO: 2;
iii) having protease resistance;
iv) showing high expression in a soluble fraction of E. coli, and
vii) not allowing purification using iminobiotin.

Embodiment 13

The modified biotin-binding protein according to any one of Embodiments 1 to 12, showing a biotin-binding affinity lower than that of a protein comprising the amino acid sequence represented by SEQ ID NO: 2.

Embodiment 14

The modified biotin-binding protein according to any one of Embodiments 1 to 13, satisfying at least one of the following provisions a) to p):

a) the 14th asparagine residue of SEQ ID NO: 2 is not modified or is replaced with glutamine or aspartic acid;
b) the 18th serine residue of SEQ ID NO: 2 is not modified or is replaced with threonine or tyrosine;
c) the 34th tyrosine residue of SEQ ID NO: 2 is not modified or is replaced with serine or threonine;
d) the 36th serine residue of SEQ ID NO: 2 is not modified or is replaced with threonine or tyrosine;
e) the 40th aspartic acid residue of SEQ ID NO: 2 is not modified or is replaced with a residue other than asparagine;
f) the 69th tryptophan residue of SEQ ID NO: 2 is not modified;
g) the 76th serine residue of SEQ ID NO: 2 is not modified or is replaced with threonine or tyrosine;
h) the 78th threonine residue of SEQ ID NO: 2 is not modified or is replaced with serine or tyrosine;
i) the 80th tryptophan residue of SEQ ID NO: 2 is not modified;
j) the 96th tryptophan residue of SEQ ID NO: 2 is not modified;
k) the 108th tryptophan residue of SEQ ID NO: 2 is not modified;
l) the 116th aspartic acid residue of SEQ ID NO: 2 is not modified or is replaced with glutamic acid or asparagine;
m) the 46th proline residue of SEQ ID NO: 2 is not modified;
n) the 66th alanine residue of SEQ ID NO: 2 is not modified;
o) the 97th leucine residue of SEQ ID NO: 2 is not modified or is modified to isoleucine; and
p) the 113th valine residue of SEQ ID NO: 2 is not modified,
wherein the amino acid residues specified in 1) to 9) are replaced as in specified in 1) to 9).

Advantageous Effects of Invention

The present invention provides modified TM2 that can be highly expressed in E. coli and has a biotin-binding activity, the strength of which appropriately allows binding to and dissociation from biotin. The modified TM2 of the present invention can be applied to, for example, affinity chromatography for purifying biotinylated substances by immobilizing the modified TM2 to a carrier.

D116A, respectively, by biotin-agarose. Each protein was applied to a biotin-agarose column for binding, and then PBS (pH 7.4) containing 10 mM biotin was added to the column for elution. To each fractionated solution, an aliquot of 2×SDS sample buffer was added. The resulting solution was treated at 95° C. for 10 min and was subjected to SDS-PAGE, followed by Coomassie brilliant blue (CBB) staining. Sup indicates a soluble fraction before application to the column, FT indicates a column flow-through fraction, W indicates a washing fraction, and Elu indicates an eluate fraction.

Figure 2A:
Figure 2B:
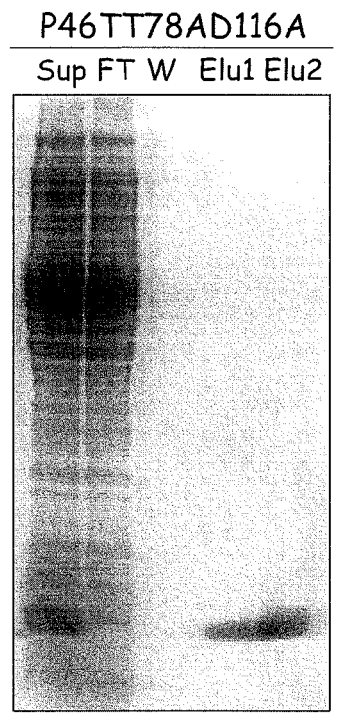
Figure 2C:
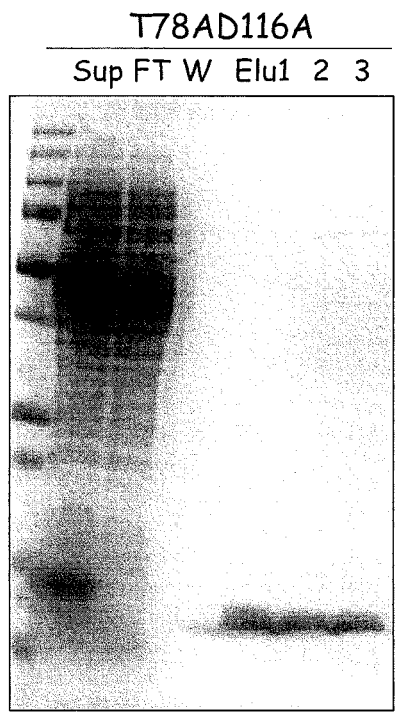
Figure 2D:
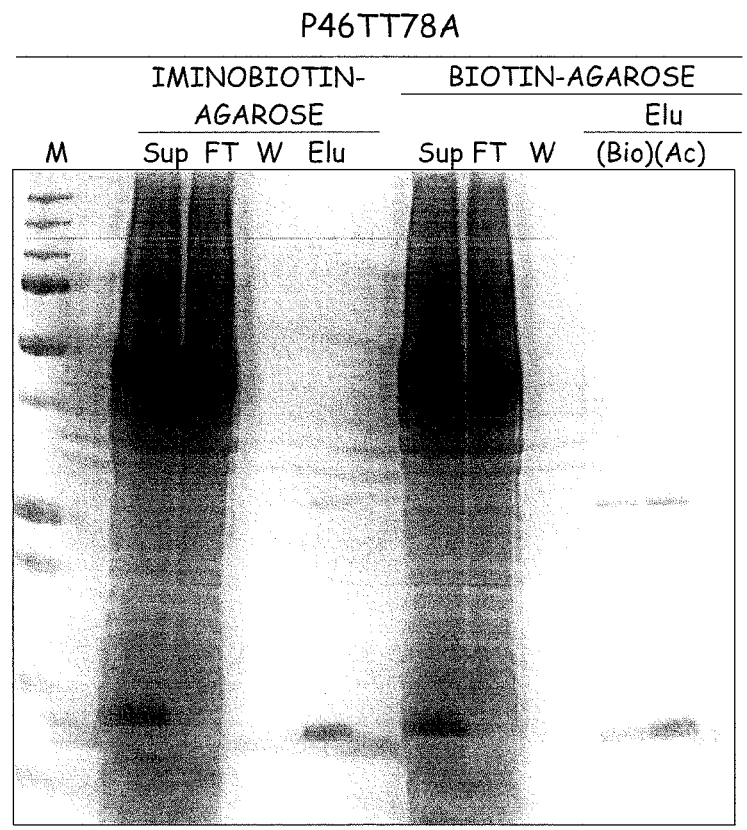

FIGS. 2A, 2B, and 2C are photographs showing purification of TM2P46TD116A, TM2P46TT78AD116A, and T78AD116A, respectively, by biotin-agarose. Elution was performed by adding PBS (pH 7.4) containing 10 mM biotin to the respective columns. FIG. 2D includes photographs showing purification of TM2P46TT78A by iminobiotin-agarose and biotin-agarose. To each fractionated solution, an aliquot of 2×SDS sample buffer was added. The resulting solution was treated at 95° C. for 10 min and was subjected to SDS-PAGE, followed by CBB staining. Sup indicates a soluble fraction before application to the column, FT indicates a column flow-through fraction, W indicates a washing fraction, and Elu indicates an eluate fraction. M indicates each molecular weight market.

Figure 3A:
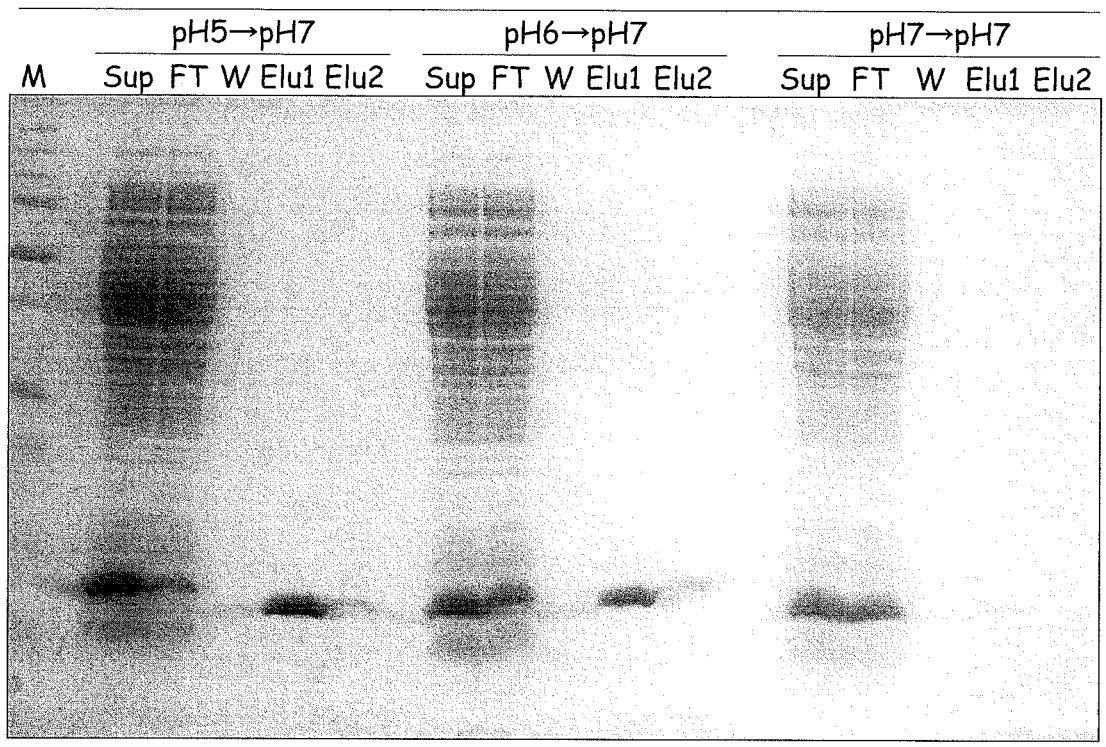
Figure 3B:
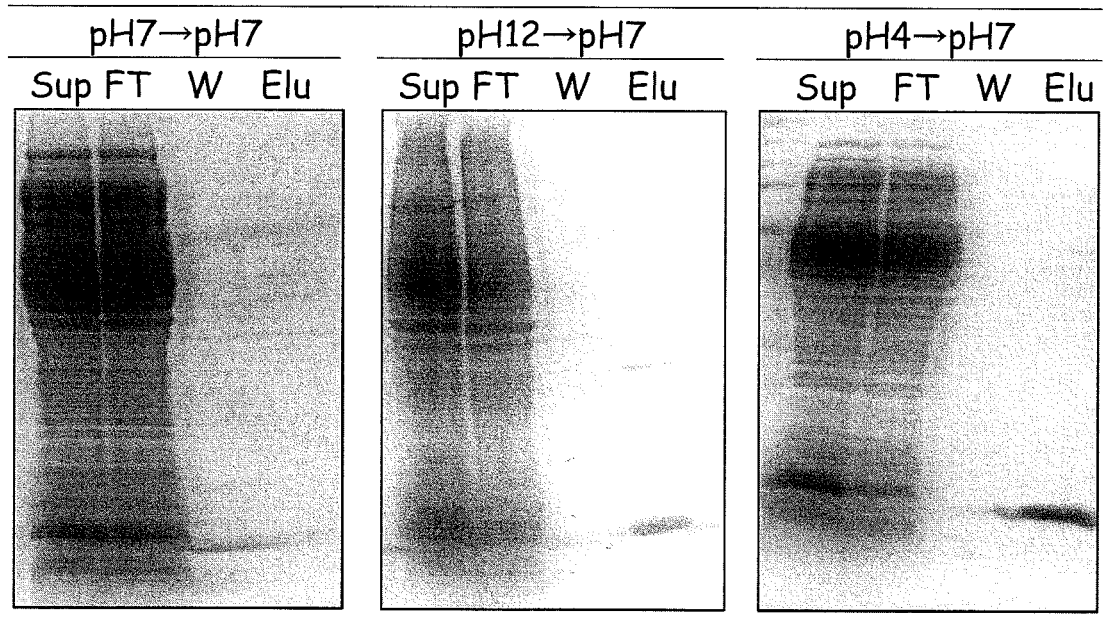

FIGS. 3A and 3B are photographs showing purification of TM2 S36A-D116A and TM2 S36A-T78A-D116A, respectively, by biotin-agarose. TM2 S36A-D116A was bound to biotin-agarose at pH 5, pH 6, or pH 7. Washing was performed using a potassium phosphate buffer (pH 4) containing 500 mM NaCl for binding at pH 5 or pH 6 and was performed using a potassium phosphate buffer (pH 7) containing 500 mM NaCl for binding at pH 7. Subsequently, elution was performed by adding 1 mL of a potassium phosphate buffer (pH 7) to the column for binding at pH 5 or pH 6 and was performed by adding 1 mL of PBS (pH 7.4) containing 10 mM of biotin for binding at pH 7. TM2 S36A-T78A-D116A was bound to biotin-agarose in a potassium phosphate buffer of pH 4 or pH 7 or in a 50 mM CAPS buffer of pH 12, and then washed and eluted by adding 1 mL of a 100 mM potassium phosphate buffer (pH 7) to each column. To each fractionated solution, an aliquot of 2×SDS sample buffer was added. The resulting solution was treated at 95° C. for 10 min and was subjected to SDS-PAGE, followed by CBB staining.

Figures 4A, 4B:
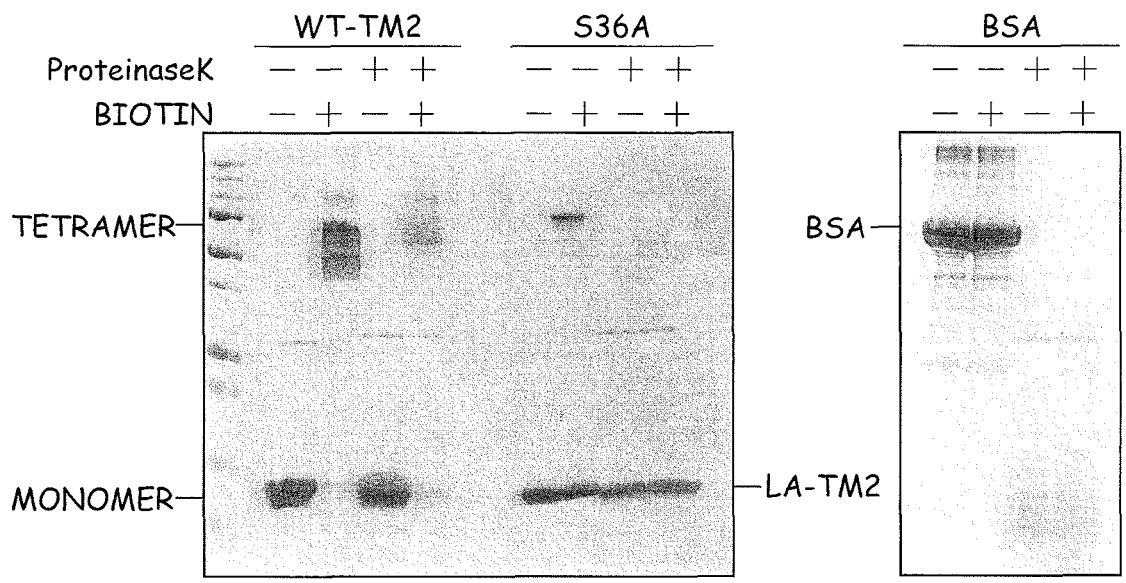
Figure 4C:
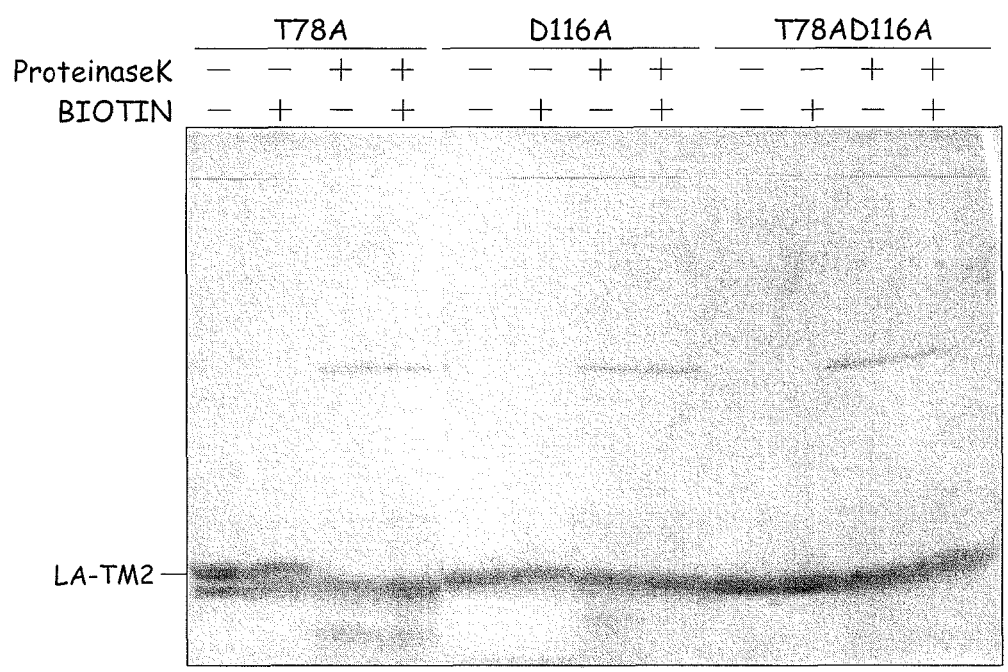

FIG. 4A includes a photograph showing protease resistance of various modified tamavidin 2 proteins (TM2 S36A) and (WT-TM2). FIG. 4B includes a photograph showing bovine serum albumin as a control (BSA). FIG. 4C includes a photograph showing protease resistance of various modified tamavidin 2 proteins (TM2 T78A), (TM2 D116A) and (TM2 T78A-D116A). Each of these modified tamavidin 2 proteins was reacted with proteinase K at 30° C. for 15 min, and a 5×SDS sample buffer was added to each reaction solution. The resulting solution was treated at 95° C. for 10 min to terminate the reaction. The samples were subjected to SDS-PAGE, followed by CBB staining.

Figures 5A, 5B:
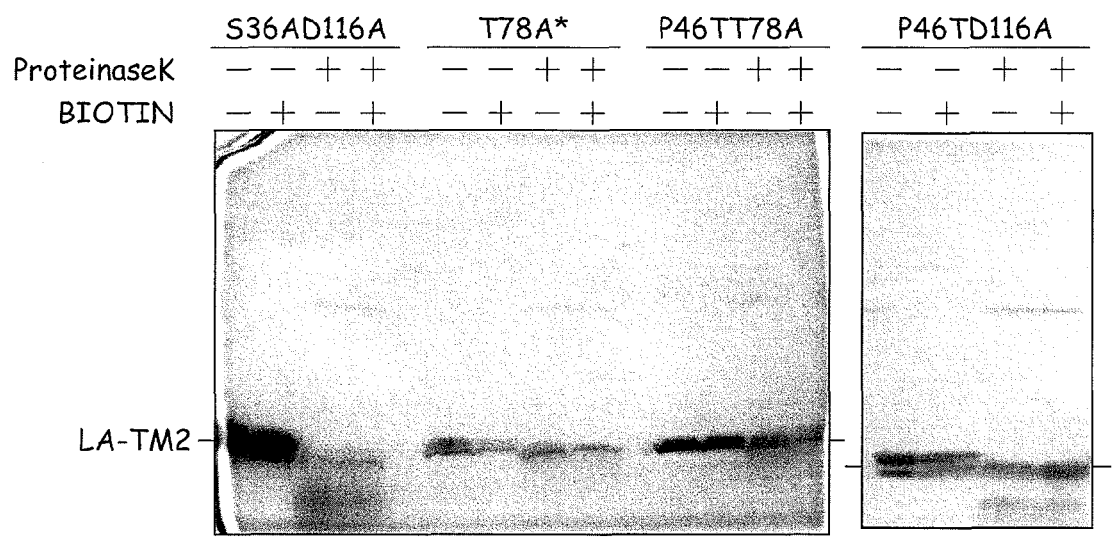
Figures 5C, 5D:
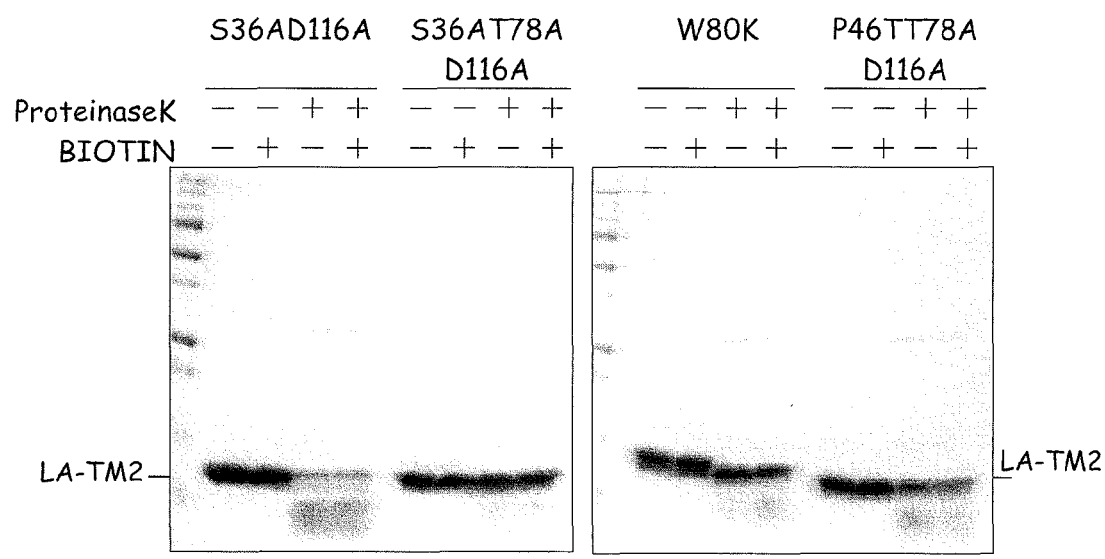

FIG. 5A includes a photograph showing protease resistance of various modified tamavidin 2 (TM2 S36A-D116A), (TM2 T78A) and (TM2P46T-T78A). FIG. 5B includes a photograph showing protease resistance of modified tamavidin 2 (TM2P46T-D116A). FIG. 5C includes a photograph showing protease resistance of various modified tamavidin 2 (TM 36A-D116A) and (TM2 36A-T78A-D116A). FIG. 5D includes a photograph showing protease resistance of various modified tamavidin 2 (TM2 W80K) and (TM2P46T-T78A-D116A). Each of these modified tamavidin 2 proteins was reacted with proteinase K at 30° C. for 15 min, and a 5×SDS sample buffer was added to each reaction solution. The resulting solution was treated at 95° C. for 10 min to terminate the reaction. The asterisked TM2 T78A sample was treated at 100° C. for 10 min to terminate the reaction. The samples were subjected to SDS-PAGE, followed by CBB staining.

Figure 6:
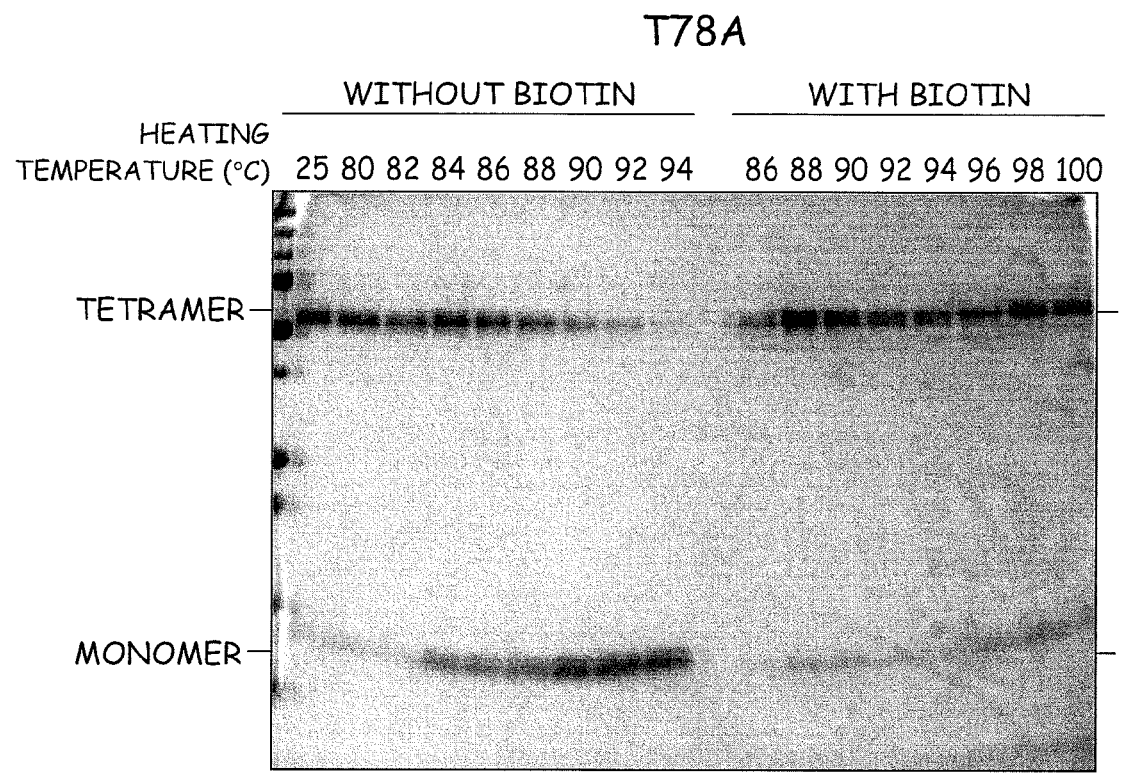

FIG. 6 is a photograph showing heat stability of TM2 T78A. TM2 T78A was heated at a predetermined temperature in a 1×SDS sample buffer for 20 min in the presence or absence of biotin, and then subjected to SDS-PAGE, followed by CBB staining.

Figure 7:

FIG. 7 includes photographs showing purification of biotinylated BSA by TM2 S36A-Sepharose. A sample containing an *E. coli* (TB1) cell extract and biotinylated BSA or a sample containing biotinylated BSA only was purified with TM2 S36A-Sepharose. After an aliquot of 2×SDS sample buffer was added to each solution of before the purification (total), column flow-through fraction (FT), washing fraction (W), and eluate fraction (Elu), the resulting solutions were treated at 95° C. for 10 min and were subjected to SDS-PAGE. The presence of biotinylated BSA was confirmed with a Silver staining II kit (manufactured by Wako Pure Chemical Industries, Ltd.), and elution was performed using a solution containing 5 mM biotin.

Figure 8A:
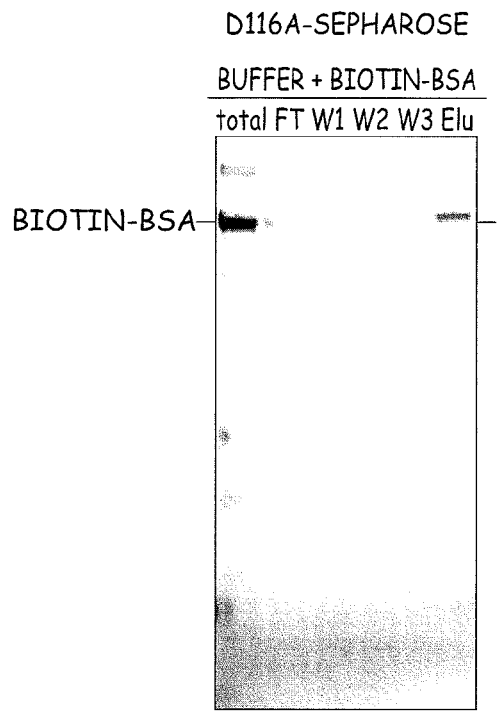
Figure 8B:
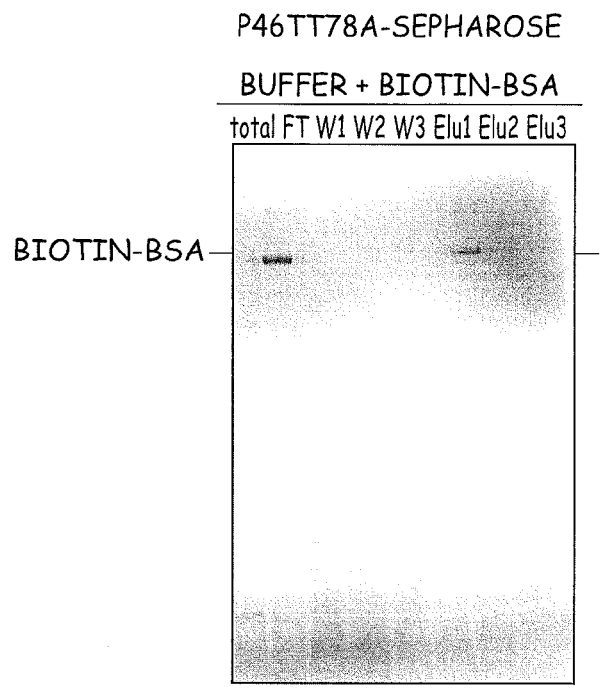
Figure 8C:
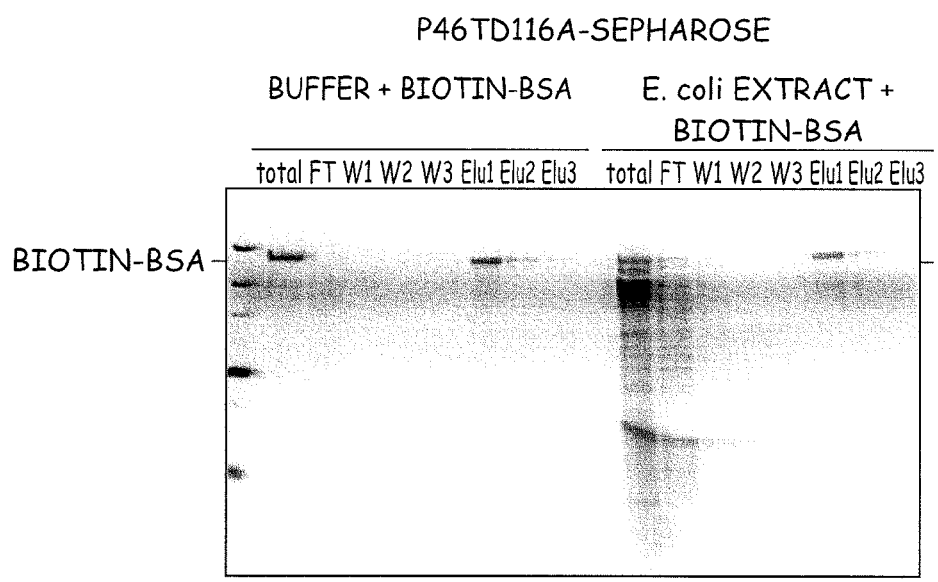

FIGS. 8A, 8B, and 8C are photographs showing purification of biotinylated BSA by TM2 D116A-Sepharose, TM2P46TT78A-Sepharose, and TM2P46TD116A-Sepharose, respectively. A sample containing biotinylated BSA only or a sample containing an *E. coli* extract and biotinylated BSA was purified with each carrier. After addition of an aliquot of 2×SDS sample buffer to each solution of before the purification (total), column flow-through fraction (FT), washing fraction (W), and eluate fraction (Elu), the resulting solutions were treated at 95° C. for 10 min and were subjected to SDS-PAGE. The presence of biotinylated BSA was confirmed with a Silver staining II kit (manufactured by Wako Pure Chemical Industries, Ltd.), and elution was performed using a solution containing 5 mM biotin.

Figure 9:
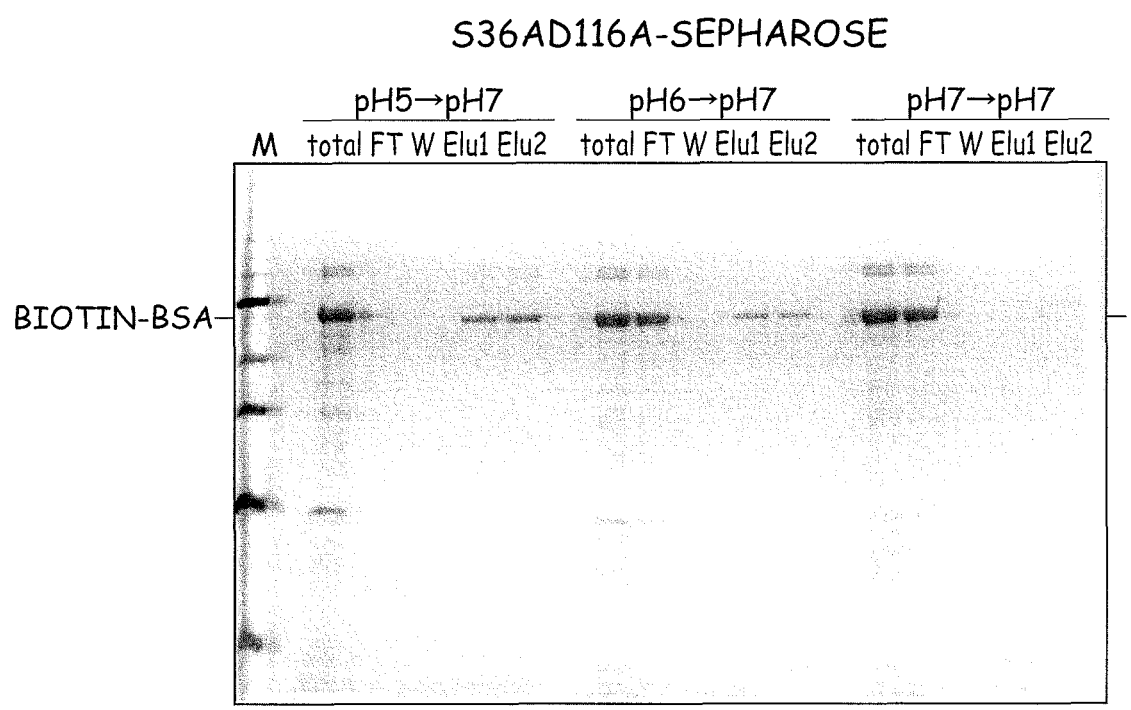

FIG. 9 is a photograph showing the pH-dependence in binding of biotinylated BSA to TM2 S36A-D116A-Sepharose. Biotinylated BSA was allowed to bind to TM2 S36A-D116A-Sepharose in a 100 mM potassium phosphate buffet (pH 5, 6, or 7) and was washed with a potassium phosphate buffer (pH 4 in the case of binding at pH 5 or 6; pH 7 in the case of binding at pH 7) containing 500 mM NaCl, and then biotinylated BSA was eluted by adding a potassium phosphate buffer (pH 7) to the column. After addition of an aliquot of 2×SDS sample buffer to each solution of before the purification (total), column flow-through fraction (FT), washing fraction (W), and eluate fraction (Elu), the resulting solutions were treated at 95° C. for 10 min and were subjected to SDS-PAGE, followed by silver staining of protein using a Silver staining II kit (manufactured by Wako Pure Chemical Industries, Ltd.).

DESCRIPTION OF EMBODIMENTS

Preferred embodiments for implementing the present invention will be described below.
Tamavidin
Tamavidin is a novel biotin-binding protein discovered in an edible mushroom, *Basidiomycetes, Pleurotus cornucopiae* (WO02/072817). This reference discloses that:
the amino acid homology between tamavidin 1 and tamavidin 2 is 65.5%, and both strongly bind to biotin;

tamavidin 2 is highly expressed in a soluble fraction of *E. coli*; and culturing of *E. coli* for expressing tamavidin 2 for 4.5 hr gave about 1 mg of a recombinant protein with high purity for 50 mL of a culture medium. This is very high value compared to avidin or streptavidin known as biotin-binding proteins.

Throughout the specification, the term "tamavidin 2" refers to tamavidin 2 (TM2) or a variant thereof. The present invention provides modified TM2 that can reversibly react with biotin by modifying a specific amino acid residue of TM2 or its variant. Throughout the specification, "tamavidin 2" and "TM2" include wild-type TM2 and variants thereof, unless specifically mentioned otherwise. However, depending on the content, they may be used as general terms of wild-type TM2, variants, and modified TM2 of the present invention. TM2, which shows biotin-binding affinity, may be referred to as "biotin-binding protein" throughout the specification.

Specifically, TM2 (wild-type) may be typically a protein comprising the amino acid sequence represented by SEQ ID NO: 2 or a protein encoded by a nucleic acid comprising the nucleotide sequence represented by SEQ ID NO: 1. Alternatively, TM2 may be a protein that is a variant of the protein comprising the amino acid sequence represented by SEQ ID NO: 2 or of the protein encoded by the nucleic acid comprising the nucleotide sequence represented by SEQ ID NO: 1 and has a biotin-binding activity similar to that of tamavidin 2. The variant of TM2 may be a protein comprising an amino acid sequence having deletion, substitution, insertion, and/or addition of one or more amino acids in the amino acid sequence of SEQ ID NO: 2. The substitution may be conservative substitution. The conservative substitution refers to replacement of a specific amino acid residue with any residue having similar physicochemical features. Non-limiting examples of the conservative substitution include substitutions between amino acid residues containing aliphatic groups, such as mutual substitution between Ile, Val, Leu, and Ala; and substitutions between polar residues, such as mutual substitution between Lys and Arg, between Gln and Asp, and between Gln and Asn.

The variants by deletion, substitution, insertion, and/or addition of an amino acid or amino acids can be produced by a known technique such as site-directed mutagenesis (e.g., see Nucleic Acid Research, Vol. 10, No. 20, pp. 6487-6500, 1982, the entity thereof is incorporated therein) to a DNA encoding a wild-type protein. Throughout the specification, the term "one or more amino acids" refers to an amino acid or amino acids that can be deleted, substituted, inserted, and/or added by preferably site-directed mutagenesis. In addition, the term "one or more amino acids" in this specification may refer to one or several amino acids.

The site-directed mutagenesis can be performed, for example, with a synthetic oligonucleotide primer that is complementary to a single-strand phage DNA to be mutated and has a specific mismatch, i.e., a desired mutation. That is, a strand complementary to the phage is synthesized with the synthetic oligonucleotide as a primer, and a host cell is transformed with the resulting double-strand DNA. The transformed bacteria culture is plated on agar to form plaques of phage-containing single cells. As a result, in theory, 50% of new colonies contain phages with the mutation as a single strand, while the remaining 50% have the original sequence. The resulting plaques are hybridized with a synthetic probe labeled by kinase treatment at a temperature which allows hybridization with DNA completely identical to one having the above desired mutation, but not with DNA having the original strand. Subsequently, plaques hybridized with the probe are picked up and cultured to collect the DNA.

The deletion, substitution, insertion, and/or addition of one or more amino acids in amino acid sequence of a biologically active peptide, while retaining the activity, may be achieved by, as well as the site-directed mutagenesis described above, treating a gene with a mutagen or perforating selective cleavage of a gene, then performing deletion, substitution, insertion, and/or addition of selected nucleotides, and then performing ligation. More preferably TM2 of the present invention is a protein comprising an amino acid sequence having deletion, substitution, insertion, and/or addition of one to ten amino acids in SEQ ID NO: 2 and having biotin-binding activity.

Furthermore, the variant of TM2 may be a protein comprising an amino acid sequence having an amino acid identity of at least 80%, preferably 85% or more, 90% or more, 95% or more, 96% or more, 97% or more, 98% or more, or 99% or more, and more preferably 99.3% or more with an amino acid sequence of SEQ ID NO: 2 and having biotin-binding activity similar to that of TM2.

The percent identity between two amino acid sequences may be determined by visual inspection and mathematical calculation. Alternatively, the percent identity between two protein sequences may be determined through comparison of sequence information using a GAP computer program available from the University of Wisconsin Genetics Computer Group (UWGCG) based on the algorithm by Needleman, S. B. and Wunsch, C. D. (J. Mol. Biol., 48: 443-453, 1970). Preferred default parameters of the GAP program include: (1) scoring matrix: blosum62 described in Henikoff, S. and Henikoff, J. G., (Proc. Natl. Acad. Sci. USA 89: 10915-10919, 1992); (2) 12 gap weights; (3) 4 gap length weights; and (4) no penalty for terminal gaps.

Any other program used by persons skilled in the art may also be used for comparison of the sequences. The percent identity can be determined by, for example, comparison with the sequence information using a BLAST program described in Altschul et. al., (Nucl. Acids Res., 25, pp. 3389-3402, 1997). This program is available from the websites of National Center for Biotechnology Information (NCBI) or DNA Data Bank of Japan (DDBJ) on the Internet. The conditions (parameters) for identity search by the BLAST program is described in detail on these sites. Although these parameters can be partly modified if necessary, search is generally carried out using the default values. Alternatively, the percent identity between two amino acid sequences may be determined using a program such as genetic information processing software GENETYX Ver. 7 (available from Genetyx Corporation) or FASTA algorithm, wherein search may be carried out using the default values.

The percent identity between two nucleotide sequences can be determined by visual inspection and mathematical calculation. Preferably, such comparison is carried out through comparison of sequence information using a computer program. A particularly preferred computer program is a version 10.0 program "GAP", Wisconsin package of Genetics Computer Group (GCG, Madison, Wis.) (Devereux, et al., 1984, Nucl. Acids Res., 12: 387). The use of the "GAP" program enables comparison between two amino acid sequences and comparison between a nucleotide sequence and an amino acid sequence, in addition to comparison of two nucleotide sequences. The preferred default parameters for the "GAP" program include: (1) the GCG implementation of a unary comparison matrix (containing a value of 1 for identities and 0 for non-identities) for nucleotides, and the weighted amino acid comparison matrix of Gribskov and Burgess, Nucl. Acids Res., 14: 6745, 1986, as described in Schwartz and Dayhoff, eds., "Atlas of Polypeptide Sequence and Structure," National Biomedical Research Foundation, pp. 353-358, 1979, or other comparable comparison matrices; (2) a penalty of 30 for each gap for amino acids and an additional penalty of 1 for each symbol in each gap, or a penalty of 50 for each gap for nucleotide sequences and an additional penalty of 3 for each symbol in each gap; (3) no penalty for end gaps; and (4) no maximum penalty for long gaps. Other sequence comparison programs used by those skilled in the art can also be used. For example, the BLASTN program version 2.2.7, which is available via the National Library of Medicine (US) website: http://www.ncbi.nlm.nih.gov/blast/bl2seq/bls.html, or the UW-BLAST 2.0 algorithm can be used. Setting of the standard default parameters for the UW-BLAST 2.0 is described at the following Internet site: http://blast.wustl.edu. In addition, the BLAST algorithm uses the BLOSUM62 amino acid scoring matrix, and optional parameters that can be used are as follows: (A) inclusion of a filter to mask segments of the query sequence having low compositional complexity (determined by the SEG program of Wootton and Federhen (Computers and Chemistry, 1993); also see Wootton and Federhen, 1996, "Analysis of compositionally biased regions in sequence databases," Methods Enzymol., 266: 544-71) or segments consisting of short-periodicity internal repeats (determined by the XNU program of Claverie and States (Computers and Chemistry, 1993)), and (B) a statistical significance threshold for reporting matches against database sequences or E-score (the expected probability of matches being found merely by chance, in accordance with the statistical model (Karlin and Altschul, 1990); if the statistical significance ascribed to a match is greater than the E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The variant of TM2 may also be a protein encoded by a nucleic acid comprising a nucleotide sequence hybridizable with the complementary strand of the nucleotide sequence of SEQ ID NO: 1 under stringent conditions and having binding activity similar to that of TM2.

Herein, the term "under stringent conditions" refers to that hybridization occurs under moderately or highly stringent conditions. Specifically, moderately stringent conditions can be readily determined by those having ordinary skill in the art, e.g., on the basis of the length of DNA. The basic conditions are set forth by Sambrook, et al., Molecular Cloning: A Laboratory Manual, 3rd edition, chapters 6 and 7, Cold Spring Harbor Laboratory Press, 2001 and include the use of a prewashing solution of 5×SSC, 0.5% SDS, and 1.0 mM EDTA (pH 8.0), hybridization conditions or about 50% formamide, 2×SSC to 6×SSC, preferably 5×SSC to 6×SSC, and 0.5% SDS at about 42° C. (or other similar hybridization solutions, such as Stark's solution, in about 50% formamide at about 42° C.), and washing conditions of, for example, about 50° C. to 68° C., 0.1 to 6×SSC, and 0.1% SDS. Preferably, moderately stringent conditions include hybridization conditions (and washing conditions) at about 50° C., 6×SSC, and 0.5% SDS. Highly stringent conditions can also be readily determined by those skilled in the art, e.g., depending on the length of DNA.

In general, highly stringent conditions include hybridization at higher temperature and/or lower salt concentration (for example, containing about 0.5% of SDS and hybridization at about 65° C., 6×SSC to 0.2×SSC, preferably 6×SSC, more preferably 2×SSC, more preferably 0.2×SSC or 0.1× SSC) and/or washing, compared to the moderately stringent conditions, and also include the hybridization conditions defined above with washing at approximately 65° C. to 68° C., 0.2×SSC or 0.1×SSC, and 0.1% SDS. With regard to the hybridization and washing buffer, SSPE (1×SSPE is 0.15 M NaCl, 10 mM NaH$_2$PO$_4$, and 1.25 mM EDTA, pH 7.4) can be substituted for SSC (1×SSC is 0.15 M NaCl and 15 mM sodium citrate). The washing is performed for about 15 min to 1 hr after completion of the hybridization.

A commercially available hybridization kit including a probe that is not a radioactive substance can also be used. Specifically, hybridization with an ECL direct labeling & detection system (manufactured by Amersham) is available. For example, stringent hybridization is performed using the hybridization buffer included in the kit to which a blocking reagent and NaCl are added in concentrations of 5% (w/v) and 0.5 M, respectively, under the following conditions: at 42° C. for 4 hours and washing twice in 0.4% SDS, 0.5×SSC at 55° C. for 20 minutes and once in 2×SSC at room temperature for 5 minutes.

The biotin-binding activity of a TM2 variant can be measured by as known method, e.g., may be measured by the process using fluorescent biotin as described in Kada, et al., (Biochim. Biophys. Acta, 1427: 33-43 (1999)). This process is an assay system utilizing a property that the fluorescent intensity of fluorescent biotin is quenched by binding of the fluorescent biotin to the biotin-binding site of a biotin-binding protein. Alternatively, the biotin-binding activity of a variant protein also can be evaluated using a sensor that can measure the binding between the protein and biotin, such as a biosensor based on surface plasmon resonance principle.

Amino acid residues that are desirably not modified in the modified tamavidin of the present invention will be described below.

Modified Tamavidin (Type I) of the Present Invention

Modified TM2 of an embodiment of the present invention includes, in a protein (TM2 or TM2 (variant)) comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having a biotin-binding activity, replacement selected from the group consisting of:

1) replacement of the 36th serine residue of SEQ ID NO: 2 with an amino acid residue that does not form a hydrogen bond;

2) replacement of the 80th tryptophan residue of SEQ ID NO: 2 with a hydrophilic amino acid residue;

3) replacement of the 116th aspartic acid residue of SEQ ID NO: 2 with an amino acid residue that does not form a hydrogen bond;

4) replacement of the 46th proline residue of SEQ ID NO: 2 with a threonine, serine, or tyrosine residue and replacement of the 78th threonine residue of SEQ ID NO: 2 with an amino acid residue that does not form a hydrogen bond;

5) replacement of the 46th proline residue of SEQ ID NO: 2 with a threonine, serine, or tyrosine residue and replacement of the 116th aspartic acid residue of SEQ ID NO: 2 with an amino acid that does not form a hydrogen bond; and 6) replacement of the 46th proline residue of SEQ ID NO: 2 with a threonine, serine, or tyrosine residue, replacement of the 78th threonine residue of SEQ ID NO: 2 with an amino acid residue that does not form a hydrogen bond, and replacement of the 116th aspartic acid residue of SEQ ID NO: 2 with an amino acid that does not form a hydrogen bond.

Throughout the specification, "tamavidin 2 (TM2)" is as already defined above.

Throughout the specification, "replacement with an amino acid residue that does not form a hydrogen bond" refers to replacement with an amino acid residue that probably does not form a hydrogen bond with biotin. Examples of such replacement include, but not limited to, replacement with an amino acid having a non-polar, i.e., hydrophobic R-group, such as alanine (A), valine (V), leucine (L), isoleucine (I), methionine (M), tryptophan (W), phenylalanine (F), and proline (P), for an amino acid residue other than these amino acid residues. In Examples in this specification, modified forms in which serine, threonine, or aspartic acid is replaced with alanine (A) are described as modified TM2.

Throughout the specification, "replacement with a hydrophilic amino acid residue" refers to replacement with an amino acid residue that is generally regarded to be hydrophilic in this technical field. Specific examples of such an amino acid include, but not limited to, polar amino acids. Specific examples of the replacement include replacement with an amino acid having an R-group that is positively charged at a physiological pH, such as lysine (K), arginine (R), and histidine (H), and replacement with an amino acid having an R-group that is negatively charged at a physiological pH, such as aspartic acid (D) and glutamic acid (E). In the modified TM2 described below, tryptophan is replaced with lysine (K).

Preferred modified TM2 is:

1-a) a modified biotin-binding protein (TM2 S36A) in which the 36th serine residue of SEQ ID NO: 2 is replaced with alanine;

2-a) a modified biotin-binding protein (TM2 W80K) in which the 80th tryptophan residue of SEQ ID NO: 2 is replaced with lysine;

3-a) a modified biotin-binding protein (TM2 D116A) in which the 116th aspartic acid residue of SEQ ID NO: 2 is replaced with alanine;

4-a) a modified biotin-binding protein (TM2P46T-T78A) in which the 46th proline residue of SEQ ID NO: 2 is replaced with threonine and the 78th threonine residue of SEQ ID NO: 2 is replaced with alanine;

5-a) a modified biotin-binding protein (TM2P46T-D116A) in which the 46th proline residue of SEQ ID NO: 2 is replaced with threonine and the 116th aspartic acid residue of SEQ ID NO: 2 is replaced with alanine; or 6-a) a modified biotin-binding protein (TM2P46T-T78A-D116A) in which the 46th proline residue of SEQ ID NO: 2 is replaced with threonine, the 78th threonine residue of SEQ ID NO: 2 is replaced with alanine, and the 116th aspartic acid residue of SEQ ID NO: 2 is replaced with alanine.

Preferred modified TM2 shows at least one of the following properties:

i) allowing purification using biotin;
ii) maintaining a tetramer structure of a protein comprising the amino acid sequence represented by SEQ ID NO: 2;
iii) having protease resistance; and
iv) showing high expression in a soluble fraction of E. coli.

Throughout the specification, "allowing purification using biotin" refers to that a protein as a subject has an adequate biotin-binding ability to bind to and be dissociated from biotin and, thereby, allows purification of a biotinylated substance (e.g., biotinylated protein) using the affinity with biotin of the protein itself and/or the protein immobilized to a carrier (e.g., column) as the subject. Accordingly, the modified TM2 is low-affinity tamavidin having biotin-binding ability lower than that of wild-type TM2.

Throughout the specification, "maintaining a tetramer structure" refers to that a tetramer subunit structure possessed by natural TM2 is substantially maintained. Specifically, it refers to a state of that the molecular weight is similar to that of wild-type TM2. For example, the state can be confirmed by measuring the molecular weight of modified TM2 by fast protein liquid chromatography (FPLC) and comparing it with the molecular weight of TM2.

Throughout the specification, "having protease resistance" refers to that a protein is not enzymatically decomposed or not substantially decomposed by protease treatment. The protease treatment is performed by, for example, proteinase K treatment at 30° C. for 15 min. The term "not enzymatically decomposed" refers to that bands of a tetramer, dimer, and/or monomer of the protein can be clearly detected by SDS-PAGE after enzyme treatment, as in wild-type TM2. That is, a protein not having protease resistance is decomposed into small molecules by protease treatment, and bands of the tetramer, dimer, and monomer are not detected by SDS-PAGE after the protease treatment. However, a protein having protease resistance is not completely decomposed by protease treatment and maintains its tetramer structure. Accordingly, bands of the tetramer and/or the dimer or monomer generated by dissociation of the tetramer are detected by SDS-PAGE.

Throughout the specification, "showing high expression in a soluble fraction of E. coli" refers to that when a protein is expressed by E. coli transformed with an expression vector containing a desired gene in an appropriate culture medium at an appropriate temperature and under expression-inducing conditions, the E. coli cells produce the recombinant protein in the soluble fraction of disrupted E. coli cells in an amount that is sufficient for detection, preferably, that is the same as or more than wild-type TM2, for example, but not limited to, in an amount of 1 mg or more, preferably 5 mg or more, 10 mg or more, 15 mg or more, and most preferably 20 mg or more for 1 L of a culture solution.

"TM2 S36A" and "TM2 D116A" are each TM2 modified at a site that probably forms a hydrogen bond with biotin and are highly expressed in a soluble fraction of E. coli. These modified TM2 proteins maintain their tetramer structures and have high protease resistance. Furthermore, the biotin-binding ability of these modified TM2 proteins is decreased in a degree sufficient to cause a reversible reaction with biotin, though they are single-amino acid modified forms. Accordingly, they can very efficiently purify biotinylated protein. In addition, even if an iminobiotin column is used, these modified TM2 proteins can be very efficiently purified. Consequently, "TM2 S36A" and "TM2 D116A" can solve the problems in known low-affinity biotin-binding proteins and are therefore very excellent proteins that reversibly bind to biotin.

"TM2 W80K" is TM2 modified at a site that probably forms a hydrophobic bond with biotin by modifying the 80th tryptophan of wild-type TM2 (SEQ ID NO: 2) to lysine. TM2 W80K is highly expressed in the soluble fraction of E. coli, maintains its tetramer structure, and has high protease resistance. Furthermore, the biotin-binding ability of this modified TM2 protein is decreased to a degree sufficient to cause a reversible reaction with biotin, though it is a single-amino acid modified form, and allows highly efficient purification of biotinylated protein with acetic acid. In addition, even if an iminobiotin column is used, this modified TM2 protein can be very efficiently purified. Consequently, W80K can solve the problems in known low-affinity biotin-binding proteins and is therefore a superior protein having a property of reversibly binding to biotin.

In "TM2P46T-T78A" and "TM2P46T-D116A", the site that is probably involved in the binding between subunits of tamavidin and probably forms a hydrogen bond with biotin is modified. Investigation using homology between amino acids of TM2 and streptavidin (total amino acid homology between the both is 48%) suggested that the 55th valine (Val), the 76th threonine (Thr), the 109th leucine (Leu), and the 125th varine (Val) in streptavidin respectively correspond to the 46th proline (Pro), the 66th alanine (Ala) the 97th leucine (Leu), and the 113th valine (Val) in TM2. That is, these amino acids are probably present at the subunit binding sites in TM2. In actual measurement of the biotin-binding activity of modified TM2 having mutation introduced to these amino acids, reversible binding to biotin is detected and approximately a half of the modified forms are mixtures of the dimer and the monomer.

"TM2P46T" having modification of the 46th proline, which is probably involved in the binding between subunits of TM2, to threonine is a mutant intended to weaken the binding between subunits, but it maintains its tetramer form. In addition, the biotin-binding ability is very high, contrary to expectations, and biotinylated substances cannot be eluted even if an excess amount of biotin is added. However, in a mutant having modification of the 78th threonine or the 116th aspartic acid, which probably forms a hydrogen bond with biotin, of this TM2P46T protein to alanine, the biotin-binding ability is changed to an appropriate level to allow sufficient purification of biotinylated substances.

Furthermore, "TM2P46T-T78A-D116A" having all these mutations also can sufficiently purify biotinylated substances.

These mutants maintain the tetramer forms and have protease resistance. It has not succeeded before to provide appropriate biotin-binding ability to a biotin-binding protein by combining the modification in hydrogen bond and the modification in binding between subunits.

Modified Tamavidin (Type II) of the Present Invention

Modified TM2 of an embodiment of the present invention includes, in a protein (TM2 or TM2 (variant)) comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having to biotin-binding activity.

6) replacement of the 78th threonine residue of SEQ ID NO: 2 with an amino acid residue that does not form a hydrogen bond.

Preferred modified TM2 is:

6-a) a modified biotin-binding protein (TM2 T78A) in which the 78th threonine residue of SEQ ID NO: 2 is replaced with alanine residue.

Throughout the specification, "tamavidin 2 (TM2)" is as already defined above.

Throughout the specification, "replacement with an amino acid residue that does not form a hydrogen bond" is as already defined above.

Preferred modified TM2 shows at least one of the following properties:

i) allowing purification using biotin;
ii) maintaining a tetramer structure of a protein comprising the amino acid sequence represented by SEQ ID NO: 2;
iii) having protease resistance; and v) having heat resistance higher than that of a protein comprising the amino acid sequence represented by SEQ ID NO: 2.

Throughout the specification, "allowing purification using biotin", "maintaining a tetramer structure", and "having protease resistance" are as already defined above.

Throughout the specification, "having high heat resistance" refers to that modified TM2 has heat resistance that is comparable to or higher than that of wild-type TM2. For example, but not limited to, the Tr value (the temperature at which quantitative ratio between monomer and tetramer becomes 1:1) in heat treatment for 20 min in the presence of SDS is preferably comparable to, more preferably by 5° C. or more, most preferably by 10° C. or more higher than that of natural TM2 in the absence of biotin.

"TM2 T78A" is recovered from a soluble fraction of *E. coli* at a high ratio (about 95%) by biotin-agarose, though at a low ratio by iminobiotin-agarose, maintains its tetramer form, and has protease resistance. In addition, TM2 T78A has adequately decreased biotin-binding activity, even though it is a single-amino acid mutant like TM2 S36A and TM2 D116A, and can purify biotinylated proteins (yield: about 40% to 50%). Furthermore, TM2 T78A has a Tr value of 88° C. in the absence of biotin, which is higher than the Tr value (78° C.) of TM2 by 10° C., and the Tm value in binding with biotin is not lower than 100° C. Thus, this protein has very high heat stability.

Modified Tamavidin (Type III) of the Present Invention

Modified TM2 of an embodiment of the present invention includes, in a protein (TM2 or TM2 (variant)) comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having as biotin-binding activity, replacement selected from the group consisting of:

7) replacement of the 36th serine residue of SEQ ID NO: 2 with an amino acid residue that does not form a hydrogen bond and replacement of the 116th aspartic acid residue of SEQ ID NO: 2 with an amino acid that does not form a hydrogen bond; and 8) replacement of the 36th serine residue of SEQ ID NO: 2 with an amino acid residue that does not form a hydrogen bond, replacement of the 78th threonine residue of SEQ ID NO: 2 with an amino acid residue that does not form a hydrogen bond, and replacement of the 116th aspartic acid residue of SEQ ID NO: 2 with an amino acid that does not form a hydrogen bond.

Throughout the specification, "tamavidin 2 (TM2)" is as already defined above.

Throughout the specification, "replacement with an amino acid residue that does not form a hydrogen bond" is as already defined above.

Preferred modified TM2 is selected from the group consisting of:

7a) a modified biotin-binding protein (TM2 S36A-D116A) in which the 36th serine residue of SEQ ID NO: 2 is replaced with alanine, and the 116th aspartic acid residue of SEQ ID NO: 2 is replaced with alanine; and 8-a) a modified biotin-binding protein (TM2 S36A-T78A-D116A) in which the 36th serine residue of SEQ ID NO: 2 is replaced with alanine, the 78th threonine residue of SEQ ID NO: 2 is replaced with alanine, and the 116th aspartic acid residue of SEQ ID NO: 2 is replaced with alanine.

Preferred modified TM2 shows at least one of the following properties:

i) allowing purification using biotin;

iii) having protease resistance; and vi) binding to biotin under weak acidic conditions and not binding to biotin under neutral conditions.

Throughout the specification, "allowing purification using biotin" and "having protease resistance" are as already defined above.

The modified tamavidin in this embodiment shows specific pH-dependence. Throughout the specification, "weak acidic" refers to a hydrogen-ion exponent in the pH range of 4 to 6, and "neutral" refers to a hydrogen-ion exponent in the pH range of 7 to 8.

"TM2 S36A-D116A" is recovered from a soluble fraction of E. coli at a recovery rate of 95% and a degree of purification of 95% (after binding at pH 4 and then dissociating at pH 7), maintains its tetramer form, has protease resistance, and has very specific pH-dependence in binding to biotin. No biotin-binding protein that does not bind to biotin around a neutral (about pH 7) region has been known. This "TM2 S36A-D116A" has characteristics that absolutely different from those of known biotin-binding proteins, that is, it does not bind to biotin at all under neutral conditions (pH 7) or alkaline conditions (pH 12), but it highly efficiently binds to biotin under weak acidic conditions (about pH 4 to 6). Accordingly, the use of this modified form allows purification of a target substance under moderate conditions without causing denaturation by exposure to strong alkaline conditions.

Throughout the specification, "alkaline conditions" refer to a hydrogen-ion exponent in the pH range of 9 to 13.

"TM2 S36A-T78A-D116A" is highly expressed in a soluble fraction of E. coli, maintains the dimer structure, and has high protease resistance. "TM2 S36A-T78A-D116A" like TM2 S36A-D116A has characteristics that absolutely different from those of known biotin-binding proteins, that is, it does not bind to biotin at all under neutral conditions (pH 7), but it efficiently binds to biotin under weak acidic conditions (about pH 4 to 6). However, unlike TM2 S36A-D116A, "TM2 S36A-T78A-D116A" efficiently binds to biotin under alkaline conditions as under weak acidic conditions.

"TM2 S36A-T78A-D116A" is also characterized in that it does not bind to iminobiotin at all and, thus, cannot be purified with iminobiotin. This is the same as the property vii) in type IV described below. The meaning of "cannot be purified with iminobiotin" will be described in detail in the description of the type IV.

Modified Tamavidin (Type IV) of the Present Invention

Modified TM2 of an embodiment of the present invention includes, in a protein (TM2 or TM2 (variant)) comprising an amino acid sequence represented by SEQ ID NO: 2, an amino acid sequence having one to several amino acid mutations in the amino acid sequence of SEQ ID NO: 2, or an amino acid sequence having an identity of not less than 80% to the amino acid sequence of SEQ ID NO: 2 and having a biotin-binding activity.

9) replacement of the 78th threonine residue of SEQ ID NO: 2 with an amino acid residue that does not form a hydrogen bond and replacement of the 116th aspartic acid residue of SEQ ID NO: 2 with an amino acid that does not form as hydrogen bond.

Throughout the specification, "tamavidin 2 (TM2)" is as already defined above.

Throughout the specification, "replacement with an amino acid that does not form a hydrogen bond" is as already defined above.

Preferred modified TM2 is:

9-a) a modified biotin-binding protein (TM2 T78A-D116A) in which the 78th threonine residue of SEQ ID NO: 2 is replaced with alanine and the 116th aspartic acid residue of SEQ ID NO: 2 is replaced with alanine.

Preferred modified TM2 shows at least one of the following properties:

i) allowing purification using biotin;

ii) maintaining a tetramer structure of a protein comprising the amino acid sequence represented by SEQ ID NO: 2;

iii) having protease resistance;

iv) showing high expression in a soluble fraction of E. coli; and vii) not allowing purification using iminobiotin.

Throughout the specification, "allowing purification using biotin", "maintaining a tetramer structure", "having protease resistance", and "showing high expression in a soluble fraction of E. coli" are as already defined above.

Throughout the specification, "not allowing purification using iminobiotin" refers to that a target protein cannot be purified with iminobiotin because the target protein does not bind to iminobiotin or the target protein bound to iminobiotin cannot be eluted.

"TM2 T78A-D116A" is highly expressed in a soluble fraction of E. coli, maintains its tetramer form, and has high protease resistance. This modified form has specific characteristics that have not been known at all, that is, it can be purified by biotin very well, though it cannot be purified by iminobiotin at all.

This modified form can have, for example, the following applications. In the case of specifically labeling a cell using an antigen on the surface of the cell as a mark, the variant form described above is injected into a subject to bind to endogenous biotin in the blood of the subject. An antibody specific to the antigen is then iminobiotinylated and is introduced into the subject to label the cell with iminobiotin. Lastly, a radioisotope-labeled or fluorescence-labeled protein that strongly binds to biotin, such as avidin, streptavidin, tamavidin, is injected to the subject to specifically label the cell. In this system, the endogenous biotin level is reduced in advance by the modified form to reduce the background, and the modified form does not bind to iminobiotin, though binds to biotin, and therefore does not bind to the cell. In general, biotin-binding proteins bind to both iminobiotin and biotin. Thus, this system is nothing without such modified forms.

Modification of Amino Acid

The modified TM2 of the present invention can be obtained through modification of amino acid(s) of TM2 by a known method of performing mutation in an amino acid sequence and is not particularly limited. Preferably, modification is performed in the nucleotide sequence of nucleic acid encoding a modified protein of the present invention.

For example, in order to modify an amino acid at a specific position of an amino acid sequence, for example, a method employing PCR can be used (Higuchi, et al., (1988), Nucleic Acid Res., 16: 7351-7367; Ho, et al., (1989), Gene, 77: 51-59). That is, a desired modified form can be obtained by performing PCR using a primer containing a mismatch codon of a target mutation to produce DNA encoding the target modified form and expressing the DNA.

A modification by deletion, substitution, insertion, and/or addition of amino acid(s) can be produced by a known method, for example, implementing site-directed mutagenesis in DNA encoding a wild-type protein.

Amino Acid Residues that are Desirably not Iodine in Modified TM2 of the Present Invention The modification of amino acid residue(s) in the modified TM2 of the present invention is performed in such a manner that the modified TM2 has adequate affinity to biotin to allow purification. Incidentally, the biotin pocket of streptavidin, which is one of biotin-binding proteins, has been already elucidated. The homology between amino acid sequences of this streptavidin and TM2 is only about 50%, but the present inventors have compared amino acid sequences of TM2 and streptavidin side by side in order to obtain findings on biotin pocket of TM2.

As a result, it has been found that N14, S18, Y34, S36, D40, W69, S76, T78, W80, W96, W108, and D116 residues in TM2 respectively correspond to N23, S27, Y43, S45, N49, W79, S88, T90, W92, W108, W120, and D128 that directly interact with biotin (Weber, et al., (1989), Science, 243: 85-88) among the amino acids forming biotin pocket of streptavidin and are well conserved. It is believed that TM2 and the biotin-binding pocket of streptavidin have very similar structures, and these amino acid residues are highly involved in binding to biotin.

The 49th asparagine (N) of streptavidin corresponds to the 40th aspartic acid (D) in TM2, is only exception. The inventors have found that the biotin-binding ability increases in TM2 D40N TM2 having modification of the 40th aspartic acid to asparagine, as in streptavidin. Accordingly, the biotin-binding ability of the modified form in which the 40th aspartic acid is replaced with asparagine is too strong, and it is not desirable to use the TM2 D40N TM2 in the present invention.

In particular, four tryptophan residues (W69, W80, W96, and W108) are believed to play important roles in the structure of biotin pocket and are desirably not modified excluding substituents specified in the modified forms described above. Alternatively, in modification of these residues, it is desirable to modify the residues to amino acids having similar properties or structures, for example, to phenylalanine (F) so as to maintain the binding with biotin.

At the same time, it is preferred that other amino acids that are believed to be involved in binding with biotin, i.e., amino acid residues (N14, S18, Y34, S36, S76, T78, and D116) that are believed to directly interact with biotin in TM2 not be modified, except for the substitution specified in the above description. Alternatively, in modification of these residues, it is desirable to modify the residues to amino acids having similar properties or structures so as to maintain the binding with biotin. Examples of such modification include modification of asparagine (N14) to glutamine (Q) or aspartic acid (D), preferably to glutamine; modification of aspartic acid (D40) to amino acid residue other than asparagine (N); modification of serine (S18, S36, or S76) to threonine (T) or tyrosine (Y), preferably to threonine; modification of tyrosine (Y34) to serine (S) or threonine (T), preferably to threonine; modification of threonine (T78) to serine (S) or tyrosine (Y), preferably serine; and modification of aspartic acid (D116) to glutamic acid (F) or asparagine (N), preferably to glutamic acid.

It is also preferred that P46, A66, L97, and V113, which are present at subunit-binding site, not be modified, except for substitution specified in the above description. In modification of these residues, it is desirable to modify the residues to amino acids having similar properties or structures so as to maintain the binding with biotin. For example, leucine (L97) is desirably modified to isoleucine.

In all cases, the amino acid residues specified in the above-mentioned 1) to 9) are respectively substituted as specified in 1) to 9).

Nucleic Acid Encoding Modified TM2 Protein

The present invention provides a nucleic acid encoding the modified TM2 protein of the present invention. In the nucleotide sequence of such a nucleic acid, the nucleotide sequence (SEQ ID NO: 1) of TM2 is modified to a nucleotide sequence encoding the modified amino acids of the modified TM2 protein. The modified nucleotide sequence is not limited as long as it encodes amino acids after modification. Examples of the modified nucleotide sequence include nucleic acids having modified nucleotide sequences for modification of the present invention, wherein the nucleic acids are those comprising the nucleotide sequence of SEQ ID NO: 1 (hereinafter referred to as "TM2 gene") or those hybridizable with the complementary strands thereof under stringent conditions and encoding proteins having biotin-binding activity suitable for binding to and dissociation from biotin.

Preferably, the nucleic acid of the present invention encodes any of the amino acid sequences of SEQ ID NOs: 4, 6, 8, 10, 12, 14, 16, 18, and 20. More preferably, the nucleic acid of the present invention includes any one of the nucleotide sequences of SEQ ID NOs: 3, 5, 7, 9, 11, 13, 15, 17, and 19.

Vector Containing Nucleic Acid of the Present Invention

The present invention provides a vector containing a nucleic acid encoding a modified TM2 protein, preferably an expression vector for expressing a modified TM2 protein.

The nucleic acid encoding the modified TM2 protein of the present invention is as described in the section "Nucleic acid encoding modified TM2 protein", but is not particularly limited. It is desirable that a promoter functioning in a desired host and a terminator be disposed upstream and downstream, respectively, of the nucleic acid encoding the modified TM2 protein.

The vector of the present invention is preferably an expression vector. The expression vector includes a unit replicable in a desired host, for example, a replication origin, and may include a drug-resistant marker gene for selecting a desired host cell, in addition to an expression unit (promoter, modified TM2-encoding region, and terminator) as described above. The host is not particularly limited, but is preferably *E. coli*. The expression vector may contain an appropriate expression regulatory system such as a lactose repressor system.

Modified TM2-Immobilized Carrier

The present invention provides a carrier to which the modified TM2 protein of the present invention is immobilized.

Any known material constituting a carrier can be used. Examples of such a material include, but not limited to, cellulose, Teflon, nitrocellulose, agarose, highly crosslinked agarose, dextran, chitosan, polystyrene, polyacrylamide, polyester, polycarbonate polyamide, polypropylene, nylon, polydivinylidene fluoride, latex, silica, glass, glass fiber, gold, platinum, silver, copper, iron, stainless steel, ferrite, silicon wafer, polyethylene, polyethyleneimine, polylactic acid, resin, polysaccharides, proteins (e.g., albumin), carbon, and combination thereof. Materials having certain strength and stable composition and showing low non-specific binding are preferred.

Examples of the shape of the solid carrier include, but not limited to, beads, magnetic beads, thin films, microcapillary tubes, filters, plates, microplates, carbon nanotubes, and sensor chips. A planar solid carrier, such as a thin film or a plate, may be provided with, for example, pits, grooves, filter bottoms, as known in the art.

In one embodiment of the present invention, the beads can have a spherical diameter in the range of about 25 nm to about 1 mm. In a preferred embodiment, the beads have a diameter in the range of about 50 nm to about 10 μm. The size of the beads can be selected depending on specific application.

The immobilization of the protein to the carrier is not particularly limited and can be achieved by a known method for immobilizing a protein to a carrier. Specific method for immobilization can be appropriately selected by those skilled in the art depending of the type of the carrier.

EXAMPLES

The present invention will now be described in more detail with reference to examples below, which are not intended to limit the technical scope of the invention. Based on description in the specification, modifications and changes will be apparent to those skilled in the art, and such modifications and changes fall within the technical scope of the invention.

Example 1

Construction and Analysis of Low Affinity Tamavidin 2 (LATM2)

1-1. Construction of Low Affinity Tamavidin 2 (Hereinafter Referred to as LATM2)

The present inventors have performed comparative investigation for amino acid sequences of streptavidin and TM2 based on the knowledge about crystal structure of streptavidin, have estimated amino acid residues interacting with biotin in TM2, and have obtained the findings that arrangement of these amino acids resembled that of amino acids interacting with biotin in streptavidin. Based on the findings, it was estimated that the 69th, 80th, 96th, and 108th tryptophan residues in the amino acid sequence of TM2 were amino acids hydrophobically binding to biotin and that the 14th asparagine, the 18th serine, the 34th tyrosine, the 36th serine, the 76th serine, the 78th threonine, and the 116th aspartic acid in the amino acid sequence of TM2 were amino acids forming hydrogen bonds with biotin. The results of the investigation show that the 46th proline, the 66th alanine, the 97th leucine, and the 113th valine are important for binding between subunits in TM2.

Based on these findings, amino acid mutation was introduced in TM2 in order to reduce affinity of TM2 to biotin. Mutations were introduced to tryptophan residues (the 69th, 80th, 96th, and 108th tryptophan), which probably play important roles in hydrophobic bonds with biotin, and to amino acids (the 14th asparagine, the 18th serine, the 34th tyrosine, the 36th serine, the 116th aspartic acid, the 76th serine, and the 78th threonine), which are probably involved in hydrogen bonding. Mutations were also introduced to amino acid residues (the 46th proline, the 66th alanine, the 97th leucine, and the 113th valine), which are probably important in binding between subunits.

That is, in order to construct LATM2, the following 30 TM2 modified forms were constructed:

(1) TM2 in which the 108th tryptophan was replaced with lysine (hereinafter referred to as "TM2 W108K");
(2) TM2 in which the 69th tryptophan was replaced with lysine (hereinafter referred to as "TM2 W69K");
(3) TM2 in which the 80th tryptophan was replaced with lysine (hereinafter referred to as "TM2 W80K", the nucleotide sequence is represented by SEQ ID NO: 3, the amino acid sequence is represented by SEQ ID NO: 4);
(4) TM2 in which the 36th serine was replaced with alanine (hereinafter referred to as "TM2 S36A", the nucleotide sequence is represented by SEQ ID NO: 5, the amino acid sequence is represented by SEQ ID NO: 6);
(5) TM2 in winch the 36th serine was replaced with alanine, the 78th threonine was replaced with alanine, and the 116th aspartic acid was replaced with alanine (hereinafter referred to as "TM2 S36A-T78A-D116A", the nucleotide sequence is represented by SEQ ID NO: 7, the amino acid sequence is represented by SEQ ID NO: 8);
(6) TM2 in which the 14th asparagine as replaced with alanine (hereinafter referred to as "TM2 N14A");
(7) TM2 in which the 78th threonine was replaced with alanine (hereinafter referred to as "TM2 T78A", the nucleotide sequence is represented by SEQ ID NO: 9, the amino acid sequence is represented by SEQ ID NO: 10);
(8) TM2 in which the 116th aspartic acid was replaced with alanine (hereinafter referred to as "TM2 D116A", the nucleotide sequence is represented by SEQ ID NO: 11, the amino acid sequence is represented by SEQ ID NO: 12);
(9) TM2 in which the 66th alanine was replaced with arginine (hereinafter referred to as "TM2 A66R");
(10) TM2 in which the 46th proline was replaced with threonine and the 66th alanine was replaced with arginine (hereinafter referred to as "TM2P46T-A66R");
(11) TM2 in which the 113th valine was replaced with arginine (hereinafter referred to as "TM2 V113R");
(12) TM2 in which the 46th proline was replaced with threonine and the 113th valine was replaced with arginine (hereinafter referred to as "TM2P46T-V113R");
(13) TM2 in which the 46th proline was replaced with threonine and the 78th threonine was replaced with alanine (hereinafter referred to as "TM2P46T-T78A", the nucleotide sequence is represented by SEQ ID NO: 13, the amino acid sequence is represented by SEQ ID NO: 14);
(14) TM2 in which the 46th proline was replaced with threonine and the 116th aspartic acid was replaced with alanine (hereinafter referred to as "TM2P46T-D116A", the nucleotide sequence is represented by SEQ ID NO: 15, the amino acid sequence is represented by SEQ ID NO: 16);
(15) TM2 in which the 46th proline was replaced with threonine, the 78th threonine was replaced with alanine, and the 116th aspartic acid was replaced with alanine (hereinafter referred to as "TM2P46T-T78A-D116A", the nucleotide sequence is represented by SEQ ID NO: 17, the amino acid sequence is represented by SEQ ID NO: 18);
(16) TM2 in which the 46th proline was replaced with threonine, the 66th alanine was replaced with arginine, and the 97th leucine was replaced with threonine (hereinafter referred to as "TM2P46T-A66R-L97T");
(17) TM2 in which the 108th tryptophan was replaced with glutamic acid (hereinafter referred to as "TM2 W108E");
(18) TM2 in which the 108th tryptophan was replaced with arginine (hereinafter referred to as "TM2 W108R");
(19) TM2 in which the 96th tryptophan was replaced with lysine (hereinafter referred to as "TM2 W96K");
(20) TM2 in which the 36th serine was replaced with alanine and the 116th aspartic acid was replaced with alanine (hereinafter referred to as "TM2 S36A-D116A", the nucleotide sequence is represented by SEQ ID NO: 19, the amino acid sequence is represented by SEQ ID NO: 20);

(21) TM2 in which the 18th serine was replaced with alanine (hereinafter referred to as "TM2 S18A");

(22) TM2 in which the 78th threonine was replaced with alanine and the 116th aspartic acid was replaced with alanine (hereinafter referred to as "TM2 T78A-D116A", the nucleotide sequence is represented by SEQ ID NO: 21, the amino acid sequence is represented by SEQ ID NO: 22);

(23) TM2 in which the 34th tyrosine was replaced with alanine (hereinafter referred to as "TM2 Y34A");

(24) TM2 in which the 46th proline was replaced with threonine (hereinafter referred to as "TM2P46T");

(25) TM2 in which the 46th proline was replaced with threonine and the 97th leucine was replaced with threonine (hereinafter referred to as "TM2P46T-L97T");

(26) TM2 in which the 46th proline was replaced with threonine, the 66th alanine was replaced with arginine, the 97th leucine was replaced with threonine, and the 113th valine was replaced with arginine (hereinafter referred to as "TM2P46T-A66R-L97T-V113R");

(27) TM2 in which the 66th alanine was replaced with arginine and the 113th valine was replaced with arginine (hereinafter referred to as "TM2 A66R-V113R");

(28) TM2 in which the 66th alanine was replaced with arginine, the 97th leucine was replaced with threonine, and the 113th valine was replaced with arginine (hereinafter referred to as "TM2 A66R-L97T-V113R");

(29) TM2 in which the 97th leucine was replaced with threonine (hereinafter referred to as "TM2 L97T"); and

(30) TM2 in which the 97th leucine was replaced with threonine and the 113th valine was replaced with arginine (hereinafter referred to as "TM2 L97T-V113R").

PCR primers to be used in mutagenesis for constructing LATM2 were designed. A primer Tm2 5' Pci having a sequence of the 5' region of a TM2 gene and a restriction enzyme PciI cleavage site (ACATGT) placed upstream of the sequence and a primer Tm2 3' Bam having a sequence of the 3' region of the TM2 gene and a restriction enzyme BamHI cleavage site (GGATCC) placed downstream of the sequence were designed. Table 1 shows sense primers containing mismatch codons for the respective tamavidin 2 modified forms and corresponding antisense primers. In Table 1, the restriction enzyme recognition sites are shown with under lines, and the mutagenesis sites are shown by dotted lines.

TABLE 1

Primer for construction of low affinity tamavidin

| Name | Sequence 5'-3' | Length | |
|---|---|---|---|
| TM2 W108K Fw | CGTGGGGACGTAAAAGAATCCACACTT | 27-mer | (SEQ ID NO: 23) |
| TM2 W108K Rv | AAGTGTGGATTCTTTTACGTCCCCACG | 27-mer | (SEQ ID NO: 24) |
| TM2 W108E Fw | CGTGGGGACGTAGAAGAATCCACACTT | 27-mer | (SEQ ID NO: 25) |
| TM2 W108E Rv | AAGTGTGGATTCTTCTACGTCCCCACG | 27-mer | (SEQ ID NO: 26) |
| TM2 W108R Fw | CGTGGGGACGTACGTGAATCCACACTT | 27-mer | (SEQ ID NO: 27) |
| TM2 W108R Rv | AAGTGTGGATTCACGTACGTCCCCACG | 27-mer | (SEQ ID NO: 28) |
| TM2 W96K Fw | ATTCTTACTCAGAAATTGTTGTCATCG | 27-mer | (SEQ ID NO: 29) |
| TM2 W96K Rv | CGATGACAACAATTTCTGAGTAAGAAT | 27-mer | (SEQ ID NO: 30) |
| TM2 S18A Fw | AATGAACTCAACGCGAAGATGGAATTG | 27-mer | (SEQ ID NO: 31) |
| TM2 S18A Rv | CAATTCCATCTTCGCGTTGAGTTCATT | 27-mer | (SEQ ID NO: 32) |
| TM2 Y34A Fw | CTCACTGGAAAGGCGCTCTCCAAAGTT | 27-mer | (SEQ ID NO: 33) |
| TM2 Y34A Rv | AACTTTGGAGAGCGCCTTTCCAGTGAG | 27-mer | (SEQ ID NO: 34) |
| TM2 S36A Fw | GGAAAGTACCTCGCGAAAGTTGGGGAT | 27-mer | (SEQ ID NO: 35) |
| TM2 S36A Rv | ATCCCCAACTTTCGCGAGGTACTTTCC | 27-mer | (SEQ ID NO: 36) |
| TM2 T78A Fw | ATTCATTCCGCTGCGACATGGAGCGGA | 27-mer | (SEQ ID NO: 37) |
| TM2 T78A Rv | TCCGCTCCATGTCGCAGCGGAATGAAT | 27-mer | (SEQ ID NO: 38) |
| TM2 D116A Fw | CTTGTGGGGAATGCGTCGTTTACAAAG | 27-mer | (SEQ ID NO: 39) |
| TM2 D116A Rv | CTTGTGGGGAATGCGTCGTTTACAAAG | 27-mer | (SEQ ID NO: 40) |
| TM2 P46T Fw | TACGTGCCCTACACCCTCTCTGGTCGC | 27-mer | (SEQ ID NO: 41) |
| TM2 P46T Rv | GCGACCAGAGAGGGTGTAGGGCACGTA | 27-mer | (SEQ ID NO: 42) |
| TM2 A66R Fw | GCTCTTGGGTGGCGTGTATCCTGGGAG | 27-mer | (SEQ ID NO: 43) |
| TM2 A66R Rv | CTCCCAGGATACACGCCACCCAAGAGC | 27-mer | (SEQ ID NO: 44) |

TABLE 1-continued

Primer for construction of low affinity tamavidin

| Name | Sequence 5'-3' | Length | |
|---|---|---|---|
| TM2 V113R Fw | GAATCCACACTTCGTGGGAATGATTCG | 27-mer | (SEQ ID NO: 45) |
| TM2 V113R Rv | CGAATCATTCCCTCGAAGTGTGGATTC | 27-mer | (SEQ ID NO: 46) |
| TM2 L97T Fw | CTTACTCAGTGGACCTTGTCATCGAGC | 27-mer | (SEQ ID NO: 47) |
| TM2 L97T Rv | GCTCGATGACAAGGTCCACTGAGTAAG | 27-mer | (SEQ ID NO: 48) |
| TM2 W69K Fw | TGGGCGGTATCCAAAGAACAGTAAA | 27-mer | (SEQ ID NO: 49) |
| TM2 W69K Rv | TTTACTGTTCTCTTTGGATACCGCCCA | 27-mer | (SEQ ID NO: 50) |
| TM2 W80K Fw | TCCGCTACGACAAAAAGCGGACAGTTC | 27-mer | (SEQ ID NO: 51) |
| TM2 W80K Rv | GAACTGTCCGCTTTTTGTCGTAGCGGA | 27-mer | (SEQ ID NO: 52) |
| TM2 N14A Fw | GGAACCTGGTACGCGGAACTCAACTCC | 27-mer | (SEQ ID NO: 53) |
| TM2 N14A Rv | GGAGTTGAGTTCCGCGTACCAGGTTCC | 27-mer | (SEQ ID NO: 54) |
| Tm2 5'Pci | AAACATGTCAGACGTTCAATCTTC | 25-mer | (SEQ ID NO: 55) |
| TM2 3'Bam | TTTTTTGGATCCTTACTTCAACCTCGGTGCG | 31-mer | (SEQ ID NO: 56) |

1-2. Gene Amplification by PCR

In order to construct an LATM2 gene, two-stage PCR was performed. In the first stage of the PCR, the 5' regions of mutant genes were amplified using a plasmid vector pTrc99A to which the TM2 gene was inserted as a template and using a primer Tm2NtermPci and antisense primers (TM2-S36A-Rv, TM2-N14A-Rv, TM2-T78A-Rv, TM2-D116A-Rv, TM2-W108K-Rv, TM2-W108E-Rv, TM2-W108R-Rv, TM2-W96K-Rv, TM2-S18A-Rv, TM2-Y34A-Rv, TM2-W69K-Rv, TM2-W80K-Rv, TM2-P46T-Rv, TM2-V113R-Rv, and TM2-L97T-Rv) containing the respective mismatch codons of the modified forms. In addition, the 3' regions of the mutant genes were amplified using a primer Tm2CtermBam and antisense primers (TM2-S36A-Fw, TM2-N14A-Fw, TM2-T78A-Fw, TM2-D116A-Fw, TM2-W108K-Fw, TM2-W108E-Fw, TM2-W108R-Fw, TM2-W96K-Fw, TM2-S18A-Fw, TM2-Y34A-Fw, TM2-W69K-Fw, TM2-W80K-Fw, TM2-P46T-Fw, TM2-V113R-Fw, and TM2-L97T-Fw) containing the respective mismatch codons.

The PCR reaction conditions are as follows. To 50 μL of a reaction solution, 500 ng of a template DNA, 5 μL of 10× Pyrobest buffer (manufactured by Takara Bio Inc.), 4 μL of each 2.5 mM dNTP, 25 pmol of each primer, and 0.5 μL of 5 U/μL of Pyrobest DNA polymerase (manufactured by Takara Bio Inc.) were added. PCR was carried out through heating of one cycle of 96° C. for 3 min, ten cycles of 96° C. for 1 min, 55° C. for 1 min, and 72° C. for 2 min, and one cycle of 72° C. for 6 min, using as Program Temp Control System PC-700 (manufactured by ASTEK Corp.). As a result, PCR products having designed sizes at the 5' region and the 3' region of the gene were obtained.

These PCR products were electrophoresed with a low-melting-point agarose (SeaPlaqueGTG, Cambrex) in a TAE buffer solution. A gel piece containing a DNA fragment was cut out, and an aliquot of 200 mM NaCl was added thereto with the gel, followed by treatment at 70° C. for 10 min to melt the gel. This sample was extracted once with phenol, once with phenol/chloroform, and then once with chloroform, followed by ethanol precipitation to collect DNA fragments of the 5' region and 3' region of the gene. The second stage of the PCR was performed using the both DNA fragments of the 5' region and 3' region of each mutant gene as templates and using primers Tm2NtermPci and Tm2CtermBam. The reaction conditions were the same as those in the first stage. As a result, about 430 bp of PCR products were obtained in all clones.

1-3. Gene Cloning

The LATM2 gene fragments obtained by the PCR were each cloned in a vector pCR4 Blunt TOPO (manufactured by Invitrogen Corp.). The ligation reaction was carried out in accordance with the instructions attached to the vector kit. Each DNA was introduced into E. coli TB1 by electroporation, and the plasmid DNA was extracted in a usual manner (Sambrook, et al., 1989, Molecular Cloning, A laboratory manual, $2^{nd}$ edition). Clones confirmed to have the insert were each analyzed by PCR with M13 primers (manufactured by Takara Bio Inc.) to determine the nucleotide sequence of each PCR product from both ends using an ABI PRISM fluorescent sequencer (Model 310 Genetic Analyzer, manufactured by Perkin Elmer, Inc.). The results showed that desired mutations were introduced into the target nucleotides.

After the confirmation of the nucleotide sequences, the plasmids were double-digested with restriction enzymes PciI and BamHI, and gel purification was performed by the same method as above for collect each DNA fragment. This fragment was ligated into E. coli expression vector, pTrc99A, digested with NcoI and BamHI in advance using a Ligation kit (manufactured by Takara Bio Inc.). The ligation product was transformed into E. coli TB1, and, in a usual manner, the plasmid DNA was extracted and analyzed by restriction enzyme analysis to confirm the presence of the inserted gene. Thus, vectors for expressing LATM2 proteins: TM2 W108K/pTrc99A, TM2 W108E/pTrc99A, TM2 W108R/pTrc99A, TM2 W69K/pTrc99A, TM2 W80K/pTrc99A, TM2 W96K/pTrc99A, TM2 S18A/pTrc99A, TM2 Y34A/pTrc99A, TM2 S36A/pTrc99A, TM2 N14A/pTrc99A, TM2 T78A/pTrc99A, TM2 D116A/pTrc99A, TM2 A66R/pTrc99A, TM2P46T/pTrc99A, TM2 L97T/pTrc99A, and TM2 V113R/pTrc99A were completed.

Furthermore, LATM2 having two amino acid mutations and LATM2 having three amino acid mutations were constructed by the method described above using expression vectors containing LATM2 genes encoding point mutations as templates and primers containing the respective mismatch codons of the modified forms. As a result, TM2 S36AD116A/pTrc99A, TM2 S36ADT78AD116A/pTrc99A, TM2 T78AD116A/pTrc99A, TM2P46TL97T/pTrc99A, TM2P46TA66RL97T/pTrc99A, TM2P46TA66RL97TV113R/pTrc99A, TM2 A66RL97T/pTrc99A, TM2P46TA66R/pTrc99A, TM2 L97TV113R/pTrc99A, TM2 A66RV113R/pTrc99A, TM2 A66RL97TV113R/pTrc99A, TM2P46TV113R/pTrc99A, TM2P46TT78A/pTrc99A, TM2P46TD116A/pTrc99A, and P46TT78AD116A/pTrc99A were completed.

1-4. Expression of LATM2 in *E. Coli*

*E. coli* BL21 transformed with each LATM2/pTrc99A was inoculated into 6 mL of an LB medium containing an antibiotic, ampicillin (final concentration: 100 μg/mL) and was shaking-cultured at 25° C. until the absorbance at 600 nm reached 0.5, followed by addition of 1 mM of IPTG and shaking culture at 25° C. overnight. The *E. coli* cells in 1 mL of the culture solution were collected by centrifugation, suspended in 1500 μL of a 100 mM phosphate buffer (pH 7), and then sonicated. The resulting disruption solution was centrifugated (15000 rpm), and the supernatant was defined as a soluble fraction.

This soluble fraction was analyzed by Western blotting. The soluble fraction and 2×SDS sample buffer (125 mM Tris-HCl pH 6.8, 10% 2-mercaptoethanol, 4% SDS, 10% sucrose, 0.01% BPB) were mixed with each other in the same amounts and were heated at 95° C. for 10 min. The resulting solution was developed by SDS-PAGE, followed by Western blotting analysis using rabbit anti-TM2 antibody (PCT/JP2006/326260) as a primary antibody and alkaline phosphatase-labeled anti-rabbit IgG antibody (manufactured by Bio-Rad Laboratories, Inc.) as a secondary antibody. As the results of Western blotting analysis, a band of approximate 15.5 kDa was detected in every *E. coli* transformed with LATM2/pTrc99A, though the band was not detected in *E. coli* transformed with a vector pTrc99A not containing the LATM2 gene. The sizes of these bands agree with the molecular weight of 15.5 kDa of a monomer estimated from the amino acid sequence of TM2.

The expression level of the soluble LATM2 protein for 1 L of a culture solution was about 20 mg in each culture solution and was a similar level to WT-TM2. However, in TM2 W108R, TM2 W96K, TM2 S18A, and TM2 Y34A, expression was hardly observed. Accordingly, they were not used for subsequent investigation.

1-5. Purification of LATM2

LATM2 was purified through a column charged with 2-iminobiotin-agarose (manufactured by Sigma-Aldrich Corp.) in accordance with the method by Hofmann, et al., (1980). IPTG was added to 25 mL of a culture solution of *E. coli* transformed with each LATM2 in a final concentration of 1 mM to induce expression. The *E. coli* cells were collected by centrifugation, suspended in 1.5 mL of 50 mM CAPS (pH 12) containing 50 mM NaCl, and then sonicated. To the supernatant of the disrupted cells, 500 μL of 2-iminobiotin-agarose was added, which was then packed in a column. The column was sufficiently washed with 50 mM CAPS (pH 12) containing 500 mM NaCl, and elution was then performed with 50 mM $NH_4OAC$ (pH 4).

Purification with biotin-agarose (manufactured by Sigma-Aldrich Corp.) was performed by the following procedure. After induced expression of 25 mL of a culture solution of *E. coli* for each LATM2, the *E. coli* cells were suspended in 1.5 mL of a 100 mM potassium phosphate buffer (pH 7.0), and then sonicated. To the supernatant of the disrupted cells, 400 μL of biotin-agarose was added, which was followed by upside-down mixing for 1 hr. The agarose was packed in a column, and the column was sufficiently washed with PBS (pH 7.4) containing 500 mM NaCl, and elution was then performed with 10 mL of PBS containing 50 mM biotin.

In TM2 S36A-T78A-D116A, the *E. coli* cells were suspended in 1.5 mL of 50 mM CAPS (pH 12) containing 50 mM NaCl, and then sonicated. To the disrupted cells, 400 μL of biotin-agarose was added, which was followed by upside-down mixing for 1 hr. The column was sufficiently washed with 50 mM CAPS (pH 12) containing 500 mM NaCl, and elution was then performed with 1 mL of PBS (pH 7.4) containing 10 mM biotin.

In TM2 S36A-D116A, the *E. coli* cells were suspended in 1.5 mL of a 100 mM potassium phosphate buffer (pH 4.0), and then sonicated. To the pupernatant of the disrupted cells, 400 μL of biotin-agarose was added. Washing was performed with a 100 mM potassium phosphate buffer (pH 4) containing 500 mM NaCl, and elution was performed with 1 mL of PBS (pH 7) containing 10 mM biotin. Biotin binding to LATM2 that has been eluted with an excess amount of biotin was removed by dialysis with a 20 mM potassium phosphate buffer overnight.

Table 2 shows the recovery rates and the degrees of purification in 2-iminobiotin-agarose and biotin-agarose. The recovery rate in Table 2 was calculated by dividing the amount of LATM2 protein after purification by the amount of LATM2 protein before purification and was expressed by percent by multiplying the quotient by 100. The degree of purification was the ratio of the amount of LATM2 protein to the total amount of proteins in the purified fraction and was expressed by percent by multiplying the ratio by 100. The recovery rates and the degrees of purification in biotin-agarose were the results after binding at pH 7 and elution with an excess amount of biotin.

TABLE 2

Recovery rate and degree of purification of LATM2

| Mutation | pTrc99A-TM2- | Iminobiotin-agarose | | | Biotin-agarose (binding at pH 7, recovery with 10 mM biotin) | | |
|---|---|---|---|---|---|---|---|
| | | Recovery rate (%) | Degree of purification (%) | Note | Recover rate (%) | Degree of purification (%) | Note |
| Inhibition of hydrophobic bonding | W108K | 30 | 95 | | 95 | 95 | |
| | W108R | low expression | low expression | | low expression | low expression | |
| | W108E | 5 | 95 | To FT | 95 | 95 | |
| | W69K | 5 | 95 | To FT | 50 | 95 | recover rate: 95% by elution with acetic acid |

TABLE 2-continued

Recovery rate and degree of purification of LATM2

| Mutation | pTrc99A-TM2- | Iminobiotin-agarose | | | Biotin-agarose (binding at pH 7, recovery with 10 mM biotin) | | |
|---|---|---|---|---|---|---|---|
| | | Recovery rate (%) | Degree of purification (%) | Note | Recover rate (%) | Degree of purification (%) | Note |
| | W80K | 95 | 95 | | 50 | 95 | recover rate: 95% by elution with acetic acid |
| | W96K | low expression | low expression | | low expression | low expression | |
| Inhibition of hydrogen bonding | S36A | 95 | 95 | | 95 | 95 | |
| | S36AD116A | 0 | 0 | | 0 | 0 | recovery rate: 95% by binding at pH 4, elution at pH 7 (without biotin) |
| | S36AT78A-D116A | 0 | 0 | | 0 | 0 | recovery rate: 95% by binding at pH 4 or 12, elution at pH 7 (without biotin) |
| | N14A | 10 | 95 | | 50 | 95 | |
| | S18A | low expression | low expression | | low expression | low expression | |
| | T78A | 10 | 95 | | 95 | 95 | |
| | D116A | 95 | 95 | | 95 | 95 | |
| | T78AD116A | 0 | 0 | To FT | 95 | 95 | |
| | Y34A | low expression | low expression | | low expression | low expression | |
| Inhibition of bonding between subunits | P46T | 95 | 95 | | 0 | 0 | not eluted |
| | P46TL97T | 95 | 95 | | 30 | 95 | recover rate: 70% by elution with acetic acid |
| | P46TA66R-L97T | 0 | 0 | To FT | 50 | 95 | |
| | P46TA66R-L97TV113R | 0 | 0 | To FT | 5 | 95 | |
| | A66R | 0 | 0 | To FT | 50 | 95 | |
| | P46TA66R | 0 | 0 | To FT | 50 | 95 | |
| | A66RL97T | 0 | 0 | To FT | 80 | 95 | |
| | A66RV113R | 0 | 0 | To FT | 0 | 0 | To FT |
| | A66RL97T-V113R | 0 | 0 | To FT | 30 | 95 | |
| | L97T | 0 | 0 | To FT | 0 | 0 | not eluted |
| | L97TV113R | 0 | 0 | To FT | 70 | 95 | |
| | V113R | 0 | 0 | To FT | 30 | 95 | |
| | P46TV113R | 0 | 0 | To FT | 50 | 95 | |
| | WT | 95 | 95 | | 0 | 0 | not eluted |
| Inhibition of bonding between subunits + inhibition of hydrogen bonding | P46TT78A | 95 | 95 | | 5 | 95 | note eluted (binding at pH 7, but hardly eluted with biotin) recovery rate: 70% by binding at pH 12, extraction with acetic acid |
| | P46TD116A | 95 | 95 | | 95 | 95 | |
| | P46TT78A-D116A | 95 | 95 | | 95 | 95 | |

In the purification using 2-iminobiotin-agarose, the recovery rates and the degrees of purification of TM2P46T, TM2 S36A, TM2 D116A, TM2P46T-T78A, TM2P46T-D116A, TM2P46T-T78A-D116A, TM2 W80K, and TM2P46T-L97T among the LATM2s were similar levels to wild-type TM2 (WT-TM2: recovery rate: 95%, degree of purification: 95%).

However, the recovery rates of TM2 W108K, TM2 N14A, TM2 T78A, TM2 W108E, and TM2 W69K in purification with 2-iminobiotin-agarose were inferior to WT, although they were able to be purified.

On the contrary, TM2 S36A-T78A-D116A, TM2 S36A-D116A, TM2 A66R, TM2P46T-A66R, TM2 T78A-D116A, TM2P46T-A66R-L97T, TM2 A66R-L97T, TM2 A66R-L97T-V113R, TM2 L97T-V113R, TM2 V113R, and TM2P46T-V113R did not bind to 2-iminobiotin-agarose (manufactured by Sigma-Aldrich Corp.) and were unsuccessfully purified with 2-iminobiotin-agarose. However, all of these LATM2s bound to biotin-agarose (manufactured by Sigma-Aldrich Corp.) and were able to be purified.

TM2P46T-A66R-L97T-V113R and TM2 A66R-V113R did not bind to both 2-iminobiotin-agarose and biotin-agarose. TM2P46T and TM2 L97T bound to biotin-agarose, but were not eluted with an excess amount of biotin, like WT-TM2. This may be due to significantly strong binding with biotin.

Figure 1A:
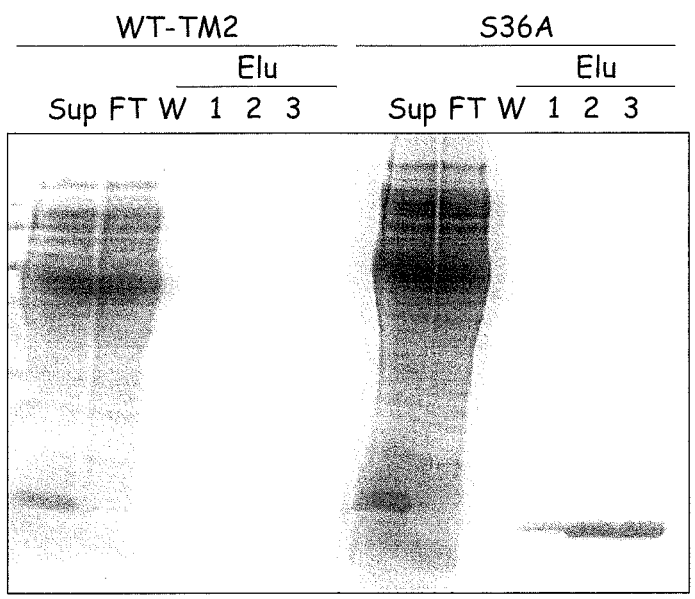
FIG. 1A includes photographs showing purification of wild-type tamavidin 2 (WT-TM2: left side) and TM2 S36A (right side) by biotin-agarose.

FIG. 1A shows the results of SDS-PAGE analysis of WT-TM2 and TM2 S36A purified with biotin-agarose. As shown in FIG. 1A, no band of WT-TM2 was observed in the flow-through (FT) lane, which indicates that WT-TM2 efficiently adsorbs to biotin-agarose. WT-TM2 was not recognized in the eluate (Elu) because its affinity with biotin was very high not to allow WT-TM2 to be eluted with an excess amount of biotin.

Figure 1B:
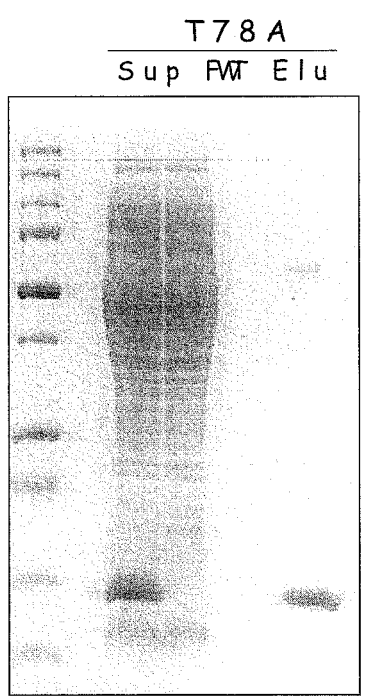
FIGS. 1B and 1C are photographs showing purification of TM2 T78A and TM2
Figure 1C:
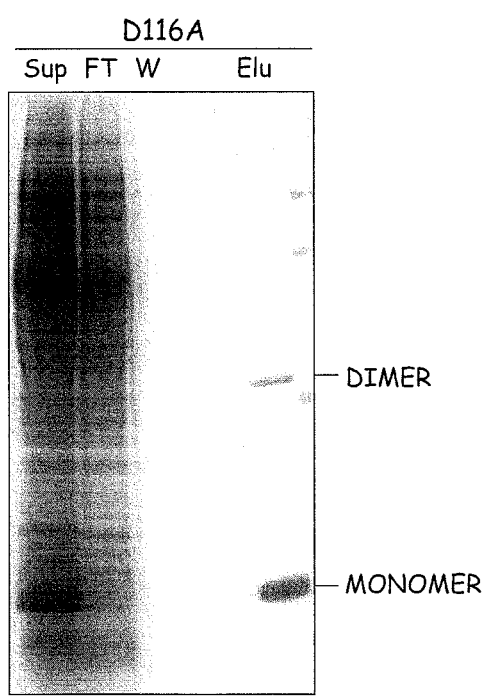

Similarly, no band of TM2 S36A was observed in the FT lane, which indicates that TM2 S36A also efficiently adsorbs to biotin-agarose. However, TM2 S36A was eluted by addition of an excess amount of biotin, and a band of TM2 S36A was detected in the Elu lane. This reversibility of the biotin binding is probably provided by a decrease in affinity with biotin as a result of the incorporation of a mutation into TM2. Other LATM2s, i.e., TM2 W108K, TM2 W108E, TM2 T78A (FIG. 1B), TM2 D116A (FIG. 1C), TM2P46T-D116A (FIG. 2A), TM2P46T-T78A-D116A (FIG. 2B), TM2 T78A-D116A (FIG. 2C), and TM2P46T-T78A (FIG. 2D) gave similar experimental results.

1-6. Specific pH-Dependence of TM2 S36A-D116A and TM2 S36A-T78A-D116A in Binding to Biotin-Agarose TM2 S36A-D116A and TM2 S36A-T78A-D116A showed pH-dependence, other LATM2s did not show, binding to biotin-agarose (manufactured by Sigma-Aldrich Corp.).

*E. coli* cells were collected from 25 mL of an *E. coli* culture solution in which expression TM2 S36A-D116A was induced with 1 mM IPTG, were suspended in 1.5 mL of a 100 mM potassium phosphate buffer (pH 7.0) or 1.5 mL of a 50 mM CAPS (pH 12.0), and then were sonicated. The disrupted cells were centrifugated, and 400 μL of biotin-agarose was added to the supernatant. As a result, the protein did not bind to biotin-agarose at all, but the protein extracted from a 100 mM potassium phosphate buffer of pH 4.0, pH 5.0, or pH 6.0 efficiently bound to biotin-agarose. Furthermore, the TM2 S36A-D116A protein was dissociated from the carrier by increasing the pH of the reaction solution to 7.0 or 12.0 and was recovered at an efficiency of 95%. That is, as shown in FIG. 3A, in the experimental system of binding with a potassium phosphate buffer of pH 5 or pH 6 and elution with a potassium phosphate of pH 7, TM2 S36A-D116A was recognized as a single band in the eluate fraction. In contrast, TM2 S36A-D116A did not bind to biotin-agarose in a potassium phosphate buffer of pH 7 and was observed in the flow-through fraction.

TM2 S36A-T78A-D116A was also investigated for its pH-dependence. The protein was suspended in a buffer of pH 4.0 or pH 12.0 and was sonicated. The disrupted cells were centrifugated and biotin-agarose was added to the supernatant to confirm its binding to biotin-agarose. However, at pH 7.0, the protein did not bind to biotin-agarose at all, like TM2 S36A-D116A. By utilizing this property, high purity TM2 S36A-T78A-D116A was obtained by binding the protein to biotin-agarose at pH 4.0 and eluting it at pH 7.0 (FIG. 3B).

1-7. Subunit Association Conditions of LATM2

In order to analyze the subunit association conditions of LATM2, the molecular weight of each LATM2s was measured by FPLC. Sephacryl S-100HR (manufactured by GE Healthcare) was used as a column, a Gel Filtration Calibration Kit LMW (manufactured by GE Healthcare) was used as molecular weight markers, and 50 mM potassium phosphate containing 500 mM NaCl was used as a buffer.

The positions of the peaks of eluted tetramer were defined to be 44 to 47 mL after injection of WT-TM2 as a control. The peak of an eluted monomer appeared at around 63 to 66 mL and the peak of an eluted dimer appeared at around 51 to 54 mL, from result of loading the molecular weight markers.

Table 3 shows the analytical results of the LATM2s.

TABLE 3

Analysis of degree of association of subunits in Sephacryl S-100HR

| Mutation | pTrc99A-TM2- | Structure (identified by FPLC) | Sephacryl (mL) |
|---|---|---|---|
| Inhibition of hydrophobic bonding | W108K | Tetramer | 45.14 |
| | W108E | tetramer, dimer (67%) | 52.30, 44.69 |
| | W69K | Tetramer | 45.09 |
| | W80K | Tetramer | 44.4 |
| Inhibition of hydrogen bonding | S36A | Tetramer | 46.17 |
| | S36AD116A | Tetramer | 46.31 |
| | S36AT78AD116A | Dimer | 51.06 |
| | N14A | Tetramer | 46.24 |
| | T78A | Tetramer | 45.71 |
| | D116A | Tetramer | 46.22 |
| | T78AD116A | Tetramer | 46.37 |
| Inhibition of bonding between subunits | P46T | Tetramer | 46.23 |
| | p46TL97T | Tetramer | 45.41 |
| | P46TA66RL97T | dimer, monomer (72.8%) | 53.95, 66.19 |
| | A66R | tetramer, monomer (30%) | 45.50, 66.15 |
| | A66RP46T | dimer, monomer (75%) | 53.47, 63.36 |
| | A66RL97T | dimer, monomer (90%) | 54.49, 65.69 |
| | A66RL97TV113R | dimer, monomer (64.8%) | 54.38, 67.21 |
| | L97TV113R | Tetramer | 45.42 |
| | V113R | Tetramer | 46.49 |
| | P46TV113R | Tetramer | 45.64 |
| | WT | Tetramer | 46.23 |
| Inhibition of bonding between subunits + inhibition of hydrogen bond | P46TT78A | Tetramer | 46.05 |
| | P46TD116A | Tetramer | 46.23 |
| | P46TT78AD116A | Tetramer | 48.24 |

It was revealed that most of the LATM2s showed peaks corresponding to their tetramers and maintained the tetramer forms, like WT-TM2. However, TM2 A66R was present partially in the monomer form (monomer: about 30% of the total), and TM2P46T-A66R, having a mutation of the 46th proline of TM2 A66R to threonine, was present almost in the monomer form (about 75% of the total). TM2P46T-A66R-L97T and TM2 A66R-L97T were present in the monomer forms in amounts of 72.8% and 90% thereof, respectively.

TM2 S36A, TM2 T78A, and TM2 D116A maintained their tetramer forms, and TM2 S36A-T78A-D116A was present in the dimer form. TM2 W108K was present in the tetramer form in an amount of 100%, but TM2 W108E was present in the form of a mixture of 33% of tetramer and 67% of dimer.

1-8. Protease Resistance of LATM2

Ten micromoles of each of the LATM2s (TM2 S36A, TM2 D116A, TM2 T78A, TM2 W80K, TM2 T78A-D116A, TM2P46T-T78A, TM2P46T-D116A, TM2 S36A-D116A, TM2 S36A-T78A-D116A, and TM2P46T-T78A-D116A) purified by biotin-agarose was subjected to a reaction in 50 mM Tris-HCl (pH 8.0) containing 5 μM Proteinase K and 5 mM $CaCl_2$ at 30° C. for 15 min. At performing it, biotin was added into some of the samples to achieve a final concentration of 1 mM. Then, an SDS buffer was added to each reaction solution, followed by heat treatment at 95° C. for 10 min to terminate the reaction. The resulting sample was subjected to SDS-PAGE, followed by CBB staining. As a control, 10 μM wild-type TM2 was reacted with 16 μM BSA under the same conditions. The results are shown in FIGS. 4 and 5.

As a result, BSA was completely decomposed in the presence of Proteinase K regardless of the presence or absence of biotin (FIG. 4B). However, wild-type (WT) TM2 (FIG. 4A), TM2-S36A (FIG. 4A), TM2 D116A (FIG. 4C), TM2 T78A (FIG. 4C, FIG. 5A), TM2 T78A-D116A (FIG. 4C), TM2P46T-T78A (FIG. 5A), TM2P46T-D116A (FIG. 5B), TM2 S36A-T78A-D116A (FIG. 5C), TM2P46T-T78A-D116A (FIG. 5D), and TM2 W80K (FIG. 5D) were hardly decomposed in the presence of Proteinase K regardless of the presence or absence of biotin and maintained molecular weights higher than those of their monomers. The results revealed that these LATM2s were stable against protease.

In TM2 S36A-D116A, approximate a half thereof was decomposed into lower molecular weight fragments in the presence of Proteinase K, but a clear band of the monomer was observed. The results showed that this LATM2 had resistance against this enzyme (FIGS. 5A and C).

1-9. Heat Resistance of LATM2s

The heat resistance of LATM2s was investigated by SDS-PAGE. Each protein was heat treated at predetermined temperatures for 20 min in an SDS sample buffer in the presence or absence of biotin and was then subjected to SDS-PAGE, followed by CBB staining. The heating temperatures in a biotin-free experimental system were 80° C., 82° C., 84° C., 86° C., 88° C., 90° C., 92° C., and 94° C., and heating temperatures in a biotin-containing experimental system were 86° C., 88° C., 90° C., 92° C., 96° C., 98° C., and 100° C.

The results are shown in FIG. 6. In FIG. 6, the left side shows the biotin-free experimental system, and the right side shows the biotin-containing experimental system. As shown in FIG. 6, the Tr value (the temperature at which the quantitative ratio between monomer and tetramer becomes 1:1) of TM2 T78A in the absence of biotin was 88° C., which was higher than the Tr value (78° C.) of wild-type TM2 by 10° C. It is believed that the association of subunits increases by the presence of biotin, and thereby the tetramer structures of WT-TM2 and TM2 T78A are stabilized to enhance the heat resistance. Actually, as shown in FIG. 6, the Tr value of TM2 T78A in the presence of biotin was higher than 100° C. Thus, it was obvious that the heat stability of TM2 T78A was enhanced.

Example 2

Purification of Biotinylated Protein by LATM2

A carrier to which LATM2 was immobilized was prepared to confirm whether or not LATM2 prepared as described above can efficiently purify a biotinylated protein.

2-1. Preparation of LATM2-Sepharose

In order to investigate whether or not a biotinylated protein can be efficiently purified with LATM2, TM2 S36A was immobilized to Sepharose to prepare TM2-S36A-Sepharose.

The resin packed in HiTrapNHS-activated HP (manufactured by GE Healthcare) was taken out and was resuspended in isopropanol. The isopropanol was removed by centrifugation (3000 rpm), followed by addition of 10 mL of cooled 1 mM HCl thereto for activation. After centrifugation (3000 rpm), the supernatant was removed, followed by addition of 10 mL of cooled Milli-Q water thereto.

The Milli-Q water was removed by centrifugation (3000 rpm), and 0.9 mL of 1.3 mg/mL of TM2 S36A was added thereto, followed by upside-down mixing at room temperature for 3 hr. After centrifugation (3000 rpm), the supernatant was removed, and 5 mL of 50 mM Tris/PBS (pH 8.0) was added thereto, followed by further upside-down mixing at room temperature for 2 hr. The Sepharose after the upside-down mixing was centrifuged (3000 rpm), and the supernatant was removed, followed by addition of 5 mL of 0.5% BSA/0.05% Tween 20 as a blocking agent thereto. The resulting mixture was further upside-down mixed for 30 min. After washing with 5 mL of PBS (pH 7.4), the carrier was resuspended in PBS (pH 7.4). The amount of TM2 S36A bound to the carrier was determined by measuring the amount of TM2 S36A remaining in the supernatants and subtracting the amount from the amount of the protein before application to the carrier. As a result, 1.01 mg of TM2 S36A, which corresponds to 86% of the protein added, was bound to the carrier.

The amounts of other LATM2sts (TM2P46T-T78A, TM2P46T-D116A, and TM2 D116A), which show similar reversible binding to biotin, bound to the carrier were also investigated. As a result, 25% of TM2P46T-T78A, i.e., 0.21 mg of 0.853 mg was bound; 93% of TM2P46T-D116A, i.e., 0.709 mg of 0.761 mg was bound; and 87% of TM2 D116A, i.e., 1.01 mg of 1.16 mg was bound.

2-2. Purification of Biotinylated BSA

Purification of a biotinylated protein was performed using the prepared TM2-S36A-Sepharose. The biotinylated protein used to be purified was bovine serum albumin (BSA) biotinylated with EZ-Link (registered trademark) NHS-biotin (linker length: 13.5 angstrom, manufactured by Pierce) (hereinafter referred to as biotinylated BSA).

An experiment was performed for purification of biotinylated BSA by modified low-affinity tamavidin of the present invention. To 75 μL of TM2-S36A-Sepharose equilibrated with a 0.1 M sodium phosphate buffer (pH 7.0), 1.66 μg of biotinylated BSA and 300 μL of an *E. coli* TB1 cell extract were added, wherein the cell extract was prepared by suspending *E. coli* TB1 cells in a 0.1 M sodium phosphate buffer (pH 7.0), sonicating the cells, centrifugating the disrupted cells, and recovering the supernatant. After upside-down mixing for 1.5 hr, TM2-S36A-Sepharose was washed with a 0.1 M sodium phosphate buffer (pH 7.0) three times, and elution was performed with 300 μL of a 0.1 M sodium phosphate buffer (pH 7.0) containing 5 mM biotin. As a control, 300 μL of a 0.1 M sodium phosphate buffer (pH 7.0) containing 1.66 μg of biotin-BSA was used instead of the cell extract. The results are shown in FIG. 7. In FIG. 7, the left side shows the experimental system in which biotinylated BSA and the cell extract were added to TM2-S36A-Sepharose, and the right side shows the experimental system in which only biotinylated BSA was added to TM2-S36A-Sepharose.

As shown in FIG. 7, biotinylated BSA present in the sample (total) before purification was almost not detected in the flow-through fraction (FT) and the washing solution (W), but was detected in the eluate (Elu). The results reveal that biotinylated BSA specifically binds to TM2-S36A-Sepharose and can be purified from various proteins in a cell extract by using TM2-S36A-Sepharose. The recovery rate and the degree of purification of biotinylated BSA were respectively 80% and 95%. Incidentally, any band assumed to be TM2-S36A was hardly detected in the eluate fraction.

Similar results were also obtained in TM2-D116A-Sepharose (FIG. 8A), TM2-P46T-T78A-Sepharose (FIG. 8B), and TM2-P46T-D116A-Sepharose (FIG. 8C) in which TM2

D116A, TM2P46T-T78A, and TM2P46T-D116A were respectively immobilized to Sepharose. That is, biotinylated BSA was able to efficiently bind to these carriers and was efficiently recovered as in the above-mentioned procedure. FIGS. 8A and B show examples of binding biotinylated BSA to TM2-D116A-Sepharose or TM2-P46T-T78A-Sepharose and recovering the biotinylated BSA at a recovery rate of 60% and a degree of purification of 95%. FIG. 8C shows examples of purifying biotinylated BSA from biotinylated BSA or a mixture of biotinylated BSA and an *E. coli* cell extract with TM2-P46T-D116A-Sepharose at a recovery rate of 80% and a degree of purification of 95%.

LATM2ss (TM2 W80K, TM2 T78A-D116A, TM2P46T-T78A-D116A), which were assumed to have reduced affinities to biotin compared to TM2 S36A, were immobilized to Sepharose and investigated for purification of biotinylated protein (BSA) from an *E. coli* crude extract. Though the purification efficiency was slightly low compared to TM2-S36A-Sepharose, biotinylated protein was purified. The recovery rate and the degree of purification were respectively 25% and 80% in TM2-W80K-Sepharose, 60% and 85% in TM2-T78A-D116A-Sepharose, and 60% and 80% in TM2P46T-T78A-D116A-Sepharose.

2-3. pH-Dependency of TM2 S36A-D116A in Binding to Biotin

TM2 S36A-D116A showed specific pH-dependency in binding to biotin-agarose (manufactured by Sigma-Aldrich Corp.) as described in the section 1-6. Accordingly, S36A-D116A-Sepharose was prepared by covalently binding TM2 S36A-D116A to Sepharose and was used for investigation of pH-dependency in purification of biotinylated protein.

S36A-D116A-Sepharose was prepared as in the section 2-1. Biotinylated BSA was bound to the prepared S36A-D116A-Sepharose in a 100 mM potassium phosphate buffer of pH 5, pH 6, or pH 7. It was sufficiently washed with a potassium phosphate buffer of pH 4 or pH 7 containing 500 mM NaCl, and the biotinylated BSA was eluted by adding a potassium phosphate buffer of pH 7 thereto. To each fraction solution, an aliquot of 2×SDS Sample Buffer was added. The resulting mixture was treated at 95° C. for 10 min and was then subjected to SDS-PAGE, followed by silver staining of the protein with a Silver staining II kit (manufactured by Wako Pure Chemical Industries, Ltd.).

FIG. 9 shows the results of SDS-PAGE of before purification (total), flow-through fraction (FT), washing solution (W), and eluate (Elu) of each sample when binding was performed at pH 5, pH 6, or pH 7. As shown in FIG. 9, a band of biotinylated BSA was confirmed in the eluate of binding at pH 5 or pH 6. Thus, S36A-D116A-Sepharose showed characteristic pH-dependency such that biotinylated protein binds thereto at pH 5 or pH 6 and is dissociated therefrom at pH 7. However, biotinylated BSA did not bind to S36A-D116A-Sepharose at pH 7.

The results revealed that TM2 S36A-D116A-Sepharose can purify biotinylated protein under significantly mild conditions of pH (e.g., binding at pH 5 and elution at pH 7).

The invention claimed is:

1. A protein comprising an amino acid sequence represented by SEQ ID NO: 2, or an amino acid sequence having an identity of not less than 95% to the amino acid sequence of SEQ ID NO: 2, the protein having replacement selected from the group consisting of:
   1) replacement of the 36th serine residue of SEQ ID NO: 2 with an amino acid residue that does not form a hydrogen bond and replacement of the 116th aspartic acid residue of SEQ ID NO: 2 with an amino acid that does not form a hydrogen bond; and
   2) replacement of the 36th serine residue of SEQ ID NO: 2 with an amino acid residue that does not form a hydrogen bond, replacement of the 78th threonine residue of SEQ ID NO: 2 with an amino acid residue that does not form a hydrogen bond, and replacement of the 116th aspartic acid residue of SEQ ID NO: 2 with an amino acid that does not form a hydrogen bond.

2. The protein according to claim 1, selected from the group consisting of:
   1-a) a modified biotin-binding protein (TM2 S36A-D116A) in which the 36th serine residue of SEQ ID NO: 2 is replaced with alanine and the 116th aspartic acid residue of SEQ ID NO: 2 is replaced with alanine; and
   2-a) a modified biotin-binding protein (TM2 S36A-T78A-D116A) in which the 36th serine residue of SEQ ID NO: 2 is replaced with alanine, the 78th threonine residue of SEQ ID NO: 2 is replaced with alanine, and the 116th aspartic acid residue of SEQ ID NO: 2 is replaced with alanine.

3. The protein according to claim 1 or 2, satisfying at least one of the following properties:
   i) allowing purification using biotin;
   ii) having protease resistance; and
   iii) binding to biotin under weak acidic conditions and not binding to biotin under neutral conditions.

4. A protein comprising an amino acid sequence represented by SEQ ID NO: 2, or an amino acid sequence having an identity of not less than 95% to the amino acid sequence of SEQ ID NO: 2, the protein comprising:
   3) replacement of the 78th threonine residue of SEQ ID NO: 2 with an amino acid residue that does not form a hydrogen bond and replacement of the 116th aspartic acid residue of SEQ ID NO: 2 with an amino acid that does not form a hydrogen bond.

5. The protein according to claim 4, wherein
   3-a) the 78th threonine residue of SEQ ID NO: 2 is replaced with alanine, and the 116th aspartic acid residue of SEQ ID NO: 2 is replaced with alanine (TM2 T78A-D116A).

6. The protein according to claim 4 or 5, satisfying at least one of the following properties:
   i) allowing purification using biotin;
   ii) maintaining a tetramer structure of a protein comprising the amino acid sequence represented by SEQ ID NO: 2;
   iii) having protease resistance;
   iv) showing high expression in a soluble fraction of *E. coli*, and
   v) not allowing purification using iminobiotin.

7. The protein according to claim 1 or 4, showing a biotin-binding affinity lower than that of a protein comprising the amino acid sequence represented by SEQ ID NO: 2.

8. The protein according to claim 1 or 4, satisfying at least one of the following provisions a) to p):
   a) the 14th asparagine residue of SEQ ID NO: 2 is not modified or is replaced with glutamine or aspartic acid;
   b) the 18th serine residue of SEQ ID NO: 2 is not modified or is replaced with threonine or tyrosine;
   c) the 34th tyrosine residue of SEQ ID NO: 2 is not modified or is replaced with serine or threonine;
   d) the 36th serine residue of SEQ ID NO: 2 is not modified or is replaced with threonine or tyrosine;
   e) the 40th aspartic acid residue of SEQ ID NO: 2 is not modified or is replaced with a residue other than asparagine;
   f) the 69th tryptophan residue of SEQ ID NO: 2 is not modified;
   g) the 76th serine residue of SEQ ID NO: 2 is not modified or is replaced with threonine or tyrosine;
   h) the 78th threonine residue of SEQ ID NO: 2 is not modified or is replaced with serine or tyrosine;
   i) the 80th tryptophan residue of SEQ ID NO: 2 is not modified;
   j) the 96th tryptophan residue of SEQ ID NO: 2 is not modified;
   k) the 108th tryptophan residue of SEQ ID NO: 2 is not modified;
   l) the 116th aspartic acid residue of SEQ ID NO: 2 is not modified or is replaced with glutamic acid or asparagine;
   m) the 46th proline residue of SEQ ID NO: 2 is not modified;
   n) the 66th alanine residue of SEQ ID NO: 2 is not modified;
   o) the 97th leucine residue of SEQ ID NO: 2 is not modified or is modified to isoleucine; and
   p) the 113th valine residue of SEQ ID NO: 2 is not modified, wherein the amino acid residues specified in 1) to 3) are replaced as in specified in 1) to 3).

9. The protein according to claim 1 or 4, comprising an amino acid sequence having an identity of not less than 98% to the amino acid sequence represented by SEQ ID NO: 2.

10. A carrier to which the protein according to claim 1 or 4 is immobilized.

11. A nucleic acid encoding the protein according to claim 1 or 4.

12. A vector containing the nucleic acid according to claim 11.

* * * * *

SEQUENCE LISTING

```
<160> NUMBER OF SEQ ID NOS: 56

<210> SEQ ID NO 1
<211> LENGTH: 840
<212> TYPE: DNA
<213> ORGANISM: Pleurotus cornucopiae
<220> FEATURE:
<221> NAME/KEY: CDS
<222> LOCATION: (226)..(651)

<400> SEQUENCE: 1
gtggactctt gcgcgggcag gtacattcac aggtcgtgca ggttgtggga gtattcagtg      60
gctcagactc ttgtgctgac gggtatagat tcacaagccg tgcaggttgt gggagtactc     120
agagggtgag tgattgaatg gaagcacatc ggcgctggtt tcaagccgag aattgaggaa     180
gtaatactcc aagccgatga gaggttacag agatcctcta ccacc atg tca gac gtt    237
                                                  Met Ser Asp Val
                                                    1 caa tct tca ctc acc gga acc tgg tac aat gaa ctc aac tcc aag atg       285
Gln Ser Ser Leu Thr Gly Thr Trp Tyr Asn Glu Leu Asn Ser Lys Met
  5              10                  15                  20 gaa ttg act gca aac aaa gac ggt act ctc act gga aag tac ctc tcc       333
Glu Leu Thr Ala Asn Lys Asp Gly Thr Leu Thr Gly Lys Tyr Leu Ser
             25                  30                  35 aaa gtt ggg gat gtc tac gtg ccc tac cca ctc tct ggt cgc tat aac       381
Lys Val Gly Asp Val Tyr Val Pro Tyr Pro Leu Ser Gly Arg Tyr Asn
         40                  45                  50 ctc caa ccc ccc gcg gga caa ggc gtc gct ctt ggg tgg gcg gta tcc       429
Leu Gln Pro Pro Ala Gly Gln Gly Val Ala Leu Gly Trp Ala Val Ser
     55                  60                  65 tgg gag aac agt aaa att cat tcc gct acg aca tgg agc gga cag ttc       477
Trp Glu Asn Ser Lys Ile His Ser Ala Thr Thr Trp Ser Gly Gln Phe
 70                  75                  80
```

```
ttc tct gag tcg tct cca gtg att ctt act cag tgg ttg ttg tca tcg    525
Phe Ser Glu Ser Ser Pro Val Ile Leu Thr Gln Trp Leu Leu Ser Ser
 85                  90                  95                 100 agc act gcg cgt ggg gac gta tgg gaa tcc aca ctt gtg ggg aat gat    573
Ser Thr Ala Arg Gly Asp Val Trp Glu Ser Thr Leu Val Gly Asn Asp
                105                 110                 115 tcg ttt aca aag acg gcg ccg act gag cag cag atc gct cat gct caa    621
Ser Phe Thr Lys Thr Ala Pro Thr Glu Gln Gln Ile Ala His Ala Gln
            120                 125                 130 ctc cat tgt cgc gca ccg agg ttg aag taa cgagggtcat cgcaaacaaa      671
Leu His Cys Arg Ala Pro Arg Leu Lys
        135                 140 ccccatcggt cttgaccggt gatccaaccc caaggtctaa tcaatgccgg atgactccat  731
ttgaggatgt gaattagttg ccatttgtat gacttgattt gtctgttgtg tagtatcgga  791
ttaagaatca catctcgtta accttcaaaa aaaaaaaaaa aaaaaaaaa              840

<210> SEQ ID NO 2
<211> LENGTH: 141
<212> TYPE: PRT
<213> ORGANISM: Pleurotus cornucopiae

<400> SEQUENCE: 2

Met Ser Asp Val Gln Ser Ser Leu Thr Gly Thr Trp Tyr Asn Glu Leu
 1               5                  10                  15

Asn Ser Lys Met Glu Leu Thr Ala Asn Lys Asp Gly Thr Leu Thr Gly
             20                  25                  30

Lys Tyr Leu Ser Lys Val Gly Asp Val Tyr Val Pro Tyr Pro Leu Ser
         35                  40                  45

Gly Arg Tyr Asn Leu Gln Pro Pro Ala Gly Gln Gly Val Ala Leu Gly
     50                  55                  60

Trp Ala Val Ser Trp Glu Asn Ser Lys Ile His Ser Ala Thr Thr Trp
 65                  70                  75                  80

Ser Gly Gln Phe Phe Ser Glu Ser Ser Pro Val Ile Leu Thr Gln Trp
                 85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 3
<211> LENGTH: 426
<212> TYPE: DNA
<213> ORGANISM: Artificial Sequence
<220> FEATURE:
<223> OTHER INFORMATION: Synthetic: TM2 W80K
<220> FEATURE:
<221> NAME/KEY: CDS
<222> LOCATION: (1)..(423)

<400> SEQUENCE: 3 atg tca gac gtt caa tct tca ctc acc gga acc tgg tac aat gaa ctc     48
Met Ser Asp Val Gln Ser Ser Leu Thr Gly Thr Trp Tyr Asn Glu Leu
 1               5                  10                  15 aac tcc aag atg gaa ttg act gca aac aaa gac ggt act ctc act gga     96
Asn Ser Lys Met Glu Leu Thr Ala Asn Lys Asp Gly Thr Leu Thr Gly
             20                  25                  30 aag tac ctc tcc aaa gtt ggg gat gtc tac gtg ccc tac cca ctc tct    144
Lys Tyr Leu Ser Lys Val Gly Asp Val Tyr Val Pro Tyr Pro Leu Ser
```

```
Lys Tyr Leu Ser Lys Val Gly Asp Val Tyr Val Pro Tyr Pro Leu Ser
             35                  40                  45 ggt cgc tat aac ctc caa ccc ccc gcg gga caa ggc gtc gct ctt ggg    192
Gly Arg Tyr Asn Leu Gln Pro Pro Ala Gly Gln Gly Val Ala Leu Gly
         50                  55                  60 tgg gcg gta tcc tgg gag aac agt aaa att cat tcc gct acg aca aaa    240
Trp Ala Val Ser Trp Glu Asn Ser Lys Ile His Ser Ala Thr Thr Lys
 65                  70                  75                  80 agc gga cag ttc ttc tct gag tcg tct cca gtg att ctt act cag tgg    288
Ser Gly Gln Phe Phe Ser Glu Ser Ser Pro Val Ile Leu Thr Gln Trp
                 85                  90                  95 ttg ttg tca tcg agc act gcg cgt ggg gac gta tgg gaa tcc aca ctt    336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa            426
Ala His Ala Gln Leu His Cys Arg Ala Pro Arg Leu Lys
    130                 135                 140
```

<210> SEQ ID NO 4
<211> LENGTH: 141
<212> TYPE: PRT
<213> ORGANISM: Artificial Sequence
<220> FEATURE:
<223> OTHER INFORMATION: Synthetic: TM2 W80K

<400> SEQUENCE: 4

```
Met Ser Asp Val Gln Ser Ser Leu Thr Gly Thr Trp Tyr Asn Glu Leu
 1               5                  10                  15

Asn Ser Lys Met Glu Leu Thr Ala Asn Lys Asp Gly Thr Leu Thr Gly
             20                  25                  30

Lys Tyr Leu Ser Lys Val Gly Asp Val Tyr Val Pro Tyr Pro Leu Ser
             35                  40                  45

Gly Arg Tyr Asn Leu Gln Pro Pro Ala Gly Gln Gly Val Ala Leu Gly
         50                  55                  60

Trp Ala Val Ser Trp Glu Asn Ser Lys Ile His Ser Ala Thr Thr Lys
 65                  70                  75                  80

Ser Gly Gln Phe Phe Ser Glu Ser Ser Pro Val Ile Leu Thr Gln Trp
                 85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140
```

<210> SEQ ID NO 5
<211> LENGTH: 426
<212> TYPE: DNA
<213> ORGANISM: Artificial Sequence
<220> FEATURE:
<223> OTHER INFORMATION: Synthetic: TM2 S36A
<220> FEATURE:
<221> NAME/KEY: CDS
<222> LOCATION: (1)..(423)

<400> SEQUENCE: 5

```
atg tca gac gtt caa tct tca ctc acc gga acc tgg tac aat gaa ctc     48
Met Ser Asp Val Gln Ser Ser Leu Thr Gly Thr Trp Tyr Asn Glu Leu
```

```

1              5                  10                    15
aac tcc aag atg gaa ttg act gca aac aaa gac ggt act ctc act gga    96
Asn Ser Lys Met Glu Leu Thr Ala Asn Lys Asp Gly Thr Leu Thr Gly
             20                  25                  30 aag tac ctc gcg aaa gtt ggg gat gtc tac gtg ccc tac cca ctc tct   144
Lys Tyr Leu Ala Lys Val Gly Asp Val Tyr Val Pro Tyr Pro Leu Ser
             35                  40                  45 ggt cgc tat aac ctc caa ccc ccc gcg gga caa ggc gtc gct ctt ggg   192
Gly Arg Tyr Asn Leu Gln Pro Pro Ala Gly Gln Gly Val Ala Leu Gly
         50                  55                  60 tgg gcg gta tcc tgg gag aac agt aaa att cat tcc gct acg aca tgg   240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg   288
Ser Gly Gln Phe Phe Ser Glu Ser Ser Pro Val Ile Leu Thr Gln Trp
                 85                  90                  95 ttg ttg tca tcg agc act gcg cgt ggg gac gta tgg gaa tcc aca ctt   336
Leu Leu Ser Ser Ser Thr Ala Arg Gly Asp Val Trp Glu Ser Thr Leu
                100                 105                 110 gtg ggg aat gat tcg ttt aca aag acg gcg ccg act gag cag cag atc   384
Val Gly Asn Asp Ser Phe Thr Lys Thr Ala Pro Thr Glu Gln Gln Ile
            115                 120                 125 gct cat gct caa ctc cat tgt cgc gca ccg agg ttg aag taa           426
Ala His Ala Gln Leu His Cys Arg Ala Pro Arg Leu Lys
        130                 135                 140

<210> SEQ ID NO 6
<211> LENGTH: 141
<212> TYPE: PRT
<213> ORGANISM: Artificial Sequence
<220> FEATURE:
<223> OTHER INFORMATION: Synthetic: TM2 S36A

<400> SEQUENCE: 6

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ala Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 7
<211> LENGTH: 426
<212> TYPE: DNA
<213> ORGANISM: Artificial Sequence
<220> FEATURE:
<223> OTHER INFORMATION: Synthetic: TM2 S36A-T78A-D116A
<220> FEATURE:
```

```
<221> NAME/KEY: CDS
<222> LOCATION: (1)..(423)

<400> SEQUENCE: 7 atg tca gac gtt caa tct tca ctc acc gga acc tgg tac aat gaa ctc       48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga       96
Asn Ser Lys Met Glu Leu Thr Ala Asn Lys Asp Gly Thr Leu Thr Gly
            20                  25                  30 aag tac ctc gcg aaa gtt ggg gat gtc tac gtg ccc tac cca ctc tct      144
Lys Tyr Leu Ala Lys Val Gly Asp Val Tyr Val Pro Tyr Pro Leu Ser
        35                  40                  45 ggt cgc tat aac ctc caa ccc ccc gcg gga caa ggc gtc gct ctt ggg      192
Gly Arg Tyr Asn Leu Gln Pro Pro Ala Gly Gln Gly Val Ala Leu Gly
50                  55                  60 tgg gcg gta tcc tgg gag aac agt aaa att cat tcc gct gcg aca tgg      240
Trp Ala Val Ser Trp Glu Asn Ser Lys Ile His Ser Ala Ala Thr Trp
65                  70                  75                  80 agc gga cag ttc ttc tct gag tcg tct cca gtg att ctt act cag tgg      288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt      336
Leu Leu Ser Ser Ser Thr Ala Arg Gly Asp Val Trp Glu Ser Thr Leu
            100                 105                 110 gtg ggg aat gcg tcg ttt aca aag acg gcg ccg act gag cag cag atc      384
Val Gly Asn Ala Ser Phe Thr Lys Thr Ala Pro Thr Glu Gln Gln Ile
        115                 120                 125 gct cat gct caa ctc cat tgt cgc gca ccg agg ttg aag taa              426
Ala His Ala Gln Leu His Cys Arg Ala Pro Arg Leu Lys
130                 135                 140

<210> SEQ ID NO 8
<211> LENGTH: 141
<212> TYPE: PRT
<213> ORGANISM: Artificial Sequence
<220> FEATURE:
<223> OTHER INFORMATION: Synthetic: TM2 S36A-T78A-D116A

<400> SEQUENCE: 8

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ala Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Ala Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Ala Ser Phe Th

```
<210> SEQ ID NO 9
<211> LENGTH: 426
<212> TYPE: DNA
<213> ORGANISM: Artificial Sequence
<220> FEATURE:
<223> OTHER INFORMATION: Synthetic: TM2 T78A
<220> FEATURE:
<221> NAME/KEY: CDS
<222> LOCATION: (1)..(423)

<400> SEQUENCE: 9 atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct     144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct gcg aca tgg     240
Trp Ala Val Ser Trp Glu Asn Ser Lys Ile His Ser Ala Ala Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc     384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
    130                 135                 140

<210> SEQ ID NO 10
<211> LENGTH: 141
<212> TYPE: PRT
<213> ORGANISM: Artificial Sequence
<220> FEATURE:
<223> OTHER INFORMATION: Synthetic: TM2 T78A

<400> SEQUENCE: 10

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Ala Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110
```

```
Val Gly Asn Asp Ser Phe Thr Lys Thr Ala Pro Thr Glu Gln Gln Ile
            115                 120                 125

Ala His Ala Gln Leu His Cys Arg Ala Pro Arg Leu Lys
    130                 135                 140

<210> SEQ ID NO 11
<211> LENGTH: 426
<212> TYPE: DNA
<213> ORGANISM: Artificial Sequence
<220> FEATURE:
<223> OTHER INFORMATION: Synthetic: TM2 D116A
<220> FEATURE:
<221> NAME/KEY: CDS
<222> LOCATION: (1)..(423)

<400> SEQUENCE: 11 atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
                20                  25                  30 aag tac ctc tcc aaa gtt ggg gat gtc tac gtg ccc tac cca ctc tct     144
Lys Tyr Leu Ser Lys Val Gly Asp Val Tyr Val Pro Tyr Pro Leu Ser
            35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
        50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gcg tcg ttt aca aag acg gcg ccg act gag cag cag atc     384
Val Gly Asn Ala Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
    130                 135                 140

<210> SEQ ID NO 12
<211> LENGTH: 141
<212> TYPE: PRT
<213> ORGANISM: Artificial Sequence
<220> FEATURE:
<223> OTHER INFORMATION: Synthetic: TM2 D116A

<400> SEQUENCE: 12

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
                20                  25                  30

Lys Tyr Leu Ser Lys Val Gly Asp Val Tyr Val Pro Tyr Pro Leu Ser
            35                  40                  45

Gly Arg Tyr Asn Leu Gln Pro Pro Ala Gly Gln Gly Val Ala Leu Gly
        50                  55                  60

Trp Ala Val Ser Trp Glu Asn Ser Lys Ile His Ser Ala Thr Thr Trp
65                  70                  75                  80
```

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Ala Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 13
<211> LENGTH: 426
<212> TYPE: DNA
<213> ORGANISM: Artificial Sequence
<220> FEATURE:
<223> OTHER INFORMATION: Synthetic: TM2 P46T-T78A
<220> FEATURE:
<221> NAME/KEY: CDS
<222> LOCATION: (1)..(423)

<400> SEQUENCE: 13

```
atg tca gac gtt caa tct tca ctc acc gga acc tgg tac aat gaa ctc        48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga        96
Asn Ser Lys Met Glu Leu Thr Ala Asn Lys Asp Gly Thr Leu Thr Gly
                20                  25                  30 aag tac ctc tcc aaa gtt ggg gat gtc tac gtg ccc tac acc ctc tct       144
Lys Tyr Leu Ser Lys Val Gly Asp Val Tyr Val Pro Tyr Thr Leu Ser
            35                  40                  45 ggt cgc tat aac ctc caa ccc ccc gcg gga caa ggc gtc gct ctt ggg       192
Gly Arg Tyr Asn Leu Gln Pro Pro Ala Gly Gln Gly Val Ala Leu Gly
        50                  55                  60 tgg gcg gta tcc tgg gag aac agt aaa att cat tcc gct gcg aca tgg       240
Trp Ala Val Ser Trp Glu Asn Ser Lys Ile His Ser Ala Ala Thr Trp
65                  70                  75                  80 agc gga cag ttc ttc tct gag tcg tct cca gtg att ctt act cag tgg       288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt       336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc       384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa              426
Ala His Ala Gln Leu His Cys Arg Ala Pro Arg Leu Lys
    130                 135                 140
```

<210> SEQ ID NO 14
<211> LENGTH: 141
<212> TYPE: PRT
<213> ORGANISM: Artificial Sequence
<220> FEATURE:
<223> OTHER INFORMATION: Synthetic: TM2 P46T-T78A

<400> SEQUENCE: 14

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
                20                  25                  30

Lys Tyr Leu Ser Lys Val Gly Asp Val Tyr Val Pro Tyr Thr Leu Ser

Gly Arg Tyr Asn Leu Gln Pro Pro Ala Gly Gln Gly Val Ala Leu Gly
        50                  55                  60

Trp Ala Val Ser Trp Glu Asn Ser Lys Ile His Ser Ala Ala Thr Trp
65                  70                  75                  80

Ser Gly Gln Phe Phe Ser Glu Ser Ser Pro Val Ile Leu Thr Gln Trp
                85                  90                  95

Leu Leu Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
        130                 135                 140

<210> SEQ ID NO 15
<211> LENGTH: 426
<212> TYPE: DNA
<213> ORGANISM: Artificial Sequence
<220> FEATURE:
<223> OTHER INFORMATION: Synthetic: TM2 P46T-D116A
<220> FEATURE:
<221> NAME/KEY: CDS
<222> LOCATION: (1)..(423)

<400> SEQUENCE: 15

```
atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
                20                  25                  30 aag tac ctc tcc aaa gtt ggg gat gtc tac gtg ccc tac acc ctc tct     144
Lys Tyr Leu Ser Lys Val Gly Asp Val Tyr Val Pro Tyr Thr Leu Ser
            35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
        50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gcg tcg ttt aca aag acg gcg ccg act gag cag cag atc     384
Val Gly Asn Ala Ser Phe Thr Lys Thr Ala Pro Thr Glu Gln Gln Ile
        115                 120                 125 gct cat gct caa ctc cat tgt cgc gca ccg agg ttg aag taa             426
Ala His Ala Gln Leu His Cys Arg Ala Pro Arg Leu Lys
        130                 135                 140
```

<210> SEQ ID NO 16
<211> LENGTH: 141
<212> TYPE: PRT
<213> ORGANISM: Artificial Sequence
<220> FEATURE:
<223> OTHER INFORMATION: Synthetic: TM2 P46T-D116A

<400> SEQUENCE: 16

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Thr Leu Ser
                35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
                100                 105                 110

Val Gly Asn Ala Ser Phe Thr Lys Thr Ala Pro Thr Glu Gln Gln Ile
            115                 120                 125

Ala His Ala Gln Leu His Cys Arg Ala Pro Arg Leu Lys
        130                 135                 140

<210> SEQ ID NO 17
<211> LENGTH: 426
<212> TYPE: DNA
<213> ORGANISM: Artificial Sequence
<220> FEATURE:
<223> OTHER INFORMATION: Synthetic: TM2 P46T-T78A-D116A
<220> FEATURE:
<221> NAME/KEY: CDS
<222> LOCATION: (1)..(423)

<400> SEQUENCE: 17 atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac acc ctc tct     144
Lys Tyr Leu Ser Lys Val Gly Asp Val Tyr Val Pro Tyr Thr Leu Ser
                35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct gcg aca tgg     240
Trp Ala Val Ser Trp Glu Asn Ser Lys Ile His Ser Ala Ala Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
                100                 105                 110 gtg ggg aat gcg tcg ttt aca aag acg gcg ccg act gag cag cag atc     384
Val Gly Asn Ala Ser Phe Thr Lys Thr Ala Pro Thr Glu Gln Gln Ile
            115                 120                 125 gct cat gct caa ctc cat tgt cgc gca ccg agg ttg aag taa             426
Ala His Ala Gln Leu His Cys Arg Ala Pro Arg Leu Lys
        130                 135                 140

<210> SEQ ID NO 18
<211> LENGTH: 141
```

```
<212> TYPE: PRT
<213> ORGANISM: Artificial Sequence
<220> FEATURE:
<223> OTHER INFORMATION: Synthetic: TM2 P46T-T78A-D116A

<400> SEQUENCE: 18

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Thr Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Ala Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Ala Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 19
<211> LENGTH: 426
<212> TYPE: DNA
<213> ORGANISM: Artificial Sequence
<220> FEATURE:
<223> OTHER INFORMATION: Synthetic: TM2 S36A-D116A
<220> FEATURE:
<221> NAME/KEY: CDS
<222> LOCATION: (1)..(423)

<400> SEQUENCE: 19 atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc gcg aaa gtt ggg gat gtc tac gtg ccc tac cca ctc tct     144
Lys Tyr Leu Ala Lys Val Gly Asp Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
            100                 105                 110 gtg ggg aat gcg tcg ttt aca aag acg gcg ccg act gag cag cag atc     384
Val Gly Asn Ala Ser Phe Thr Lys Thr Ala Pro Thr Glu Gln Gln Ile
        115                 120                 125
```

```
gct cat gct caa ctc cat tgt cgc gca ccg agg ttg aag taa          426
Ala His Ala Gln Leu His Cys Arg Ala Pro Arg Leu Lys
    130                 135                 140
```

<210> SEQ ID NO 20
<211> LENGTH: 141
<212> TYPE: PRT
<213> ORGANISM: Artificial Sequence
<220> FEATURE:
<223> OTHER INFORMATION: Synthetic: TM2 S36A-D116A

<400> SEQUENCE: 20

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ala Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Thr Ala Arg Gly Asp Val Trp Glu Ser Thr Leu
            100                 105                 110

Val Gly Asn Ala Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140
```

<210> SEQ ID NO 21
<211> LENGTH: 426
<212> TYPE: DNA
<213> ORGANISM: Artificial Sequence
<220> FEATURE:
<223> OTHER INFORMATION: Synthetic: TM2 T78A-D116A
<220> FEATURE:
<221> NAME/KEY: CDS
<222> LOCATION: (1)..(423)

<400> SEQUENCE: 21

```
atg tca gac gtt caa tct tca ctc acc gga acc tgg tac aat gaa ctc    48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga   96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct   144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg   192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct gcg aca tgg   240
Trp Ala Val Ser Trp Glu Asn Ser Lys Ile His Ser Ala Ala Thr Trp
65                  70                  75                  80 agc gga cag ttc ttc tct gag tcg tct cca gtg att ctt act cag tgg   288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt   336
Leu Leu Ser Ser Ser Thr Ala Arg Gly Asp Val Trp Glu Ser Thr Leu
```

```
Leu Leu Ser Ser Ser Thr Ala Arg Gly Asp Val Trp Glu Ser Thr Leu
            100                 105                 110 gtg ggg aat gcg tcg ttt aca aag acg gcg ccg act gag cag cag atc    384
Val Gly Asn Ala Ser Phe Thr Lys Thr Ala Pro Thr Glu Gln Gln Ile
            115                 120                 125 gct cat gct caa ctc cat tgt cgc gca ccg agg ttg aag taa             426
Ala His Ala Gln Leu His Cys Arg Ala Pro Arg Leu Lys
            130                 135                 140
```

<210> SEQ ID NO 22
<211> LENGTH: 141
<212> TYPE: PRT
<213> ORGANISM: Artificial Sequence
<220> FEATURE:
<223> OTHER INFORMATION: Synthetic: TM2 T78A-D116A

<400> SEQUENCE: 22

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Ala Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Ala Ser Phe Thr Lys Thr Ala Pro Thr Glu Gln Gln Ile
            115                 120                 125

Ala His Ala Gln Leu His Cys Arg Ala Pro Arg Leu Lys
            130                 135                 140
```

<210> SEQ ID NO 23
<211> LENGTH: 27
<212> TYPE: DNA
<213> ORGANISM: Artificial Sequence
<220> FEATURE:
<223> OTHER INFORMATION: Synthetic: forward primer for PCR Tm2 W108K

<400> SEQUENCE: 23
cgtggggacg taaaagaatc cacactt                                       27

<210> SEQ ID NO 24
<211> LENGTH: 27
<212> TYPE: DNA
<213> ORGANISM: Artificial Sequence
<220> FEATURE:
<223> OTHER INFORMATION: Synthetic: reverse primer for PCR Tm2 W108K

<400> SEQUENCE: 24
aagtgtggat tcttttacgt ccccacg                                       27

<210> SEQ ID NO 25
<211> LENGTH: 27
<212> TYPE: DNA
<213> ORGANISM: Artificial Sequence
<220> FEATURE:
<223> OTHER INFORMATION: Synthetic: forward primer for PCR Tm2 W108E

<400> SEQUENCE: 25
cgtggggacg tagaagaatc cacactt                                27

<210> SEQ ID NO 26
<211> LENGTH: 27
<212> TYPE: DNA
<213> ORGANISM: Artificial Sequence
<220> FEATURE:
<223> OTHER INFORMATION: Synthetic: reverse primer for PCR Tm2 W108E

<400> SEQUENCE: 26
aagtgtggat tcttctacgt ccccacg                                27

<210> SEQ ID NO 27
<211> LENGTH: 27
<212> TYPE: DNA
<213> ORGANISM: Artificial Sequence
<220> FEATURE:
<223> OTHER INFORMATION: Synthetic: forward primer for PCR Tm2 W108R

<400> SEQUENCE: 27
cgtggggacg tacgtgaatc cacactt                                27

<210> SEQ ID NO 28
<211> LENGTH: 27
<212> TYPE: DNA
<213> ORGANISM: Artificial Sequence
<220> FEATURE:
<223> OTHER INFORMATION: Synthetic: reverse primer for PCR Tm2 W108R

<400> SEQUENCE: 28
aagtgtggat tcacgtacgt ccccacg                                27

<210> SEQ ID NO 29
<211> LENGTH: 27
<212> TYPE: DNA
<213> ORGANISM: Artificial Sequence
<220> FEATURE:
<223> OTHER INFORMATION: Synthetic: forward primer for PCR Tm2 W96K

<400> SEQUENCE: 29
attcttactc agaaattgtt gtcatcg                                27

<210> SEQ ID NO 30
<211> LENGTH: 27
<212> TYPE: DNA
<213> ORGANISM: Artificial Sequence
<220> FEATURE:
<223> OTHER INFORMATION: Synthetic: reverse primer for PCR Tm2 W96K

<400> SEQUENCE: 30
cgatgacaac aatttctgag taagaat                                27

<210> SEQ ID NO 31
<211> LENGTH: 27
<212> TYPE: DNA
<213> ORGANISM: Artificial Sequence
<220> FEATURE:
<223> OTHER INFORMATION: Synthetic: forward primer for PCR Tm2 S18A

<400> SEQUENCE: 31
aatgaactca acgcgaagat ggaattg                                27

<210> SEQ ID NO 32

```
<211> LENGTH: 27
<212> TYPE: DNA
<213> ORGANISM: Artificial Sequence
<220> FEATURE:
<223> OTHER INFORMATION: Synthetic: reverse primer for PCR Tm2 S18A

<400> SEQUENCE: 32
caattccatc ttcgcgttga gttcatt                                              27

<210> SEQ ID NO 33
<211> LENGTH: 27
<212> TYPE: DNA
<213> ORGANISM: Artificial Sequence
<220> FEATURE:
<223> OTHER INFORMATION: Synthetic: forward primer for PCR Tm2 Y34A

<400> SEQUENCE: 33
ctcactggaa aggcgctctc caaagtt                                              27

<210> SEQ ID NO 34
<211> LENGTH: 27
<212> TYPE: DNA
<213> ORGANISM: Artificial Sequence
<220> FEATURE:
<223> OTHER INFORMATION: Synthetic: reverse primer for PCR Tm2 Y34A

<400> SEQUENCE: 34
aactttggag agcgcctttc cagtgag                                              27

<210> SEQ ID NO 35
<211> LENGTH: 27
<212> TYPE: DNA
<213> ORGANISM: Artificial Sequence
<220> FEATURE:
<223> OTHER INFORMATION: Synthetic: forward primer for PCR Tm2 S36A

<400> SEQUENCE: 35
ggaaagtacc tcgcgaaagt tggggat                                              27

<210> SEQ ID NO 36
<211> LENGTH: 27
<212> TYPE: DNA
<213> ORGANISM: Artificial Sequence
<220> FEATURE:
<223> OTHER INFORMATION: Synthetic: reverse primer for PCR Tm2 S36A

<400> SEQUENCE: 36
atccccaact ttcgcgaggt actttcc                                              27

<210> SEQ ID NO 37
<211> LENGTH: 27
<212> TYPE: DNA
<213> ORGANISM: Artificial Sequence
<220> FEATURE:
<223> OTHER INFORMATION: Synthetic: forward primer for PCR Tm2 T78A

<400> SEQUENCE: 37
attcattccg ctgcgacatg gagcgga                                              27

<210> SEQ ID NO 38
<211> LENGTH: 27
<212> TYPE: DNA
<213> ORGANISM: Artificial Sequence
<220> FEATURE:
<223> OTHER INFORMATION: Synthetic: reverse primer for PCR Tm2 T78A

<400> SEQUENCE: 38
```
tccgctccat gtcgcagcgg aatgaat                                              27

<210> SEQ ID NO 39
<211> LENGTH: 27
<212> TYPE: DNA
<213> ORGANISM: Artificial Sequence
<220> FEATURE:
<223> OTHER INFORMATION: Synthetic: forward primer for PCR Tm2 D116A

<400> SEQUENCE: 39
cttgtgggga atgcgtcgtt tacaaag                                              27

<210> SEQ ID NO 40
<211> LENGTH: 27
<212> TYPE: DNA
<213> ORGANISM: Artificial Sequence
<220> FEATURE:
<223> OTHER INFORMATION: Synthetic: reverse primer for PCR Tm2 D116A

<400> SEQUENCE: 40
ctttgtaaac gacgcattcc ccacaag                                              27

<210> SEQ ID NO 41
<211> LENGTH: 27
<212> TYPE: DNA
<213> ORGANISM: Artificial Sequence
<220> FEATURE:
<223> OTHER INFORMATION: Synthetic: forward primer for PCR Tm2 P46T

<400> SEQUENCE: 41
tacgtgccct acaccctctc tggtcgc                                              27

<210> SEQ ID NO 42
<211> LENGTH: 27
<212> TYPE: DNA
<213> ORGANISM: Artificial Sequence
<220> FEATURE:
<223> OTHER INFORMATION: Synthetic: reverse primer for PCR Tm2 P46T

<400> SEQUENCE: 42
gcgaccagag agggtgtagg gcacgta                                              27

<210> SEQ ID NO 43
<211> LENGTH: 27
<212> TYPE: DNA
<213> ORGANISM: Artificial Sequence
<220> FEATURE:
<223> OTHER INFORMATION: Synthetic: forward primer for PCR Tm2 A66R

<400> SEQUENCE: 43
gctcttgggt ggcgtgtatc ctgggag                                              27

<210> SEQ ID NO 44
<211> LENGTH: 27
<212> TYPE: DNA
<213> ORGANISM: Artificial Sequence
<220> FEATURE:
<223> OTHER INFORMATION: Synthetic: reverse primer for PCR Tm2 A66R

<400> SEQUENCE: 44
ctcccaggat acacgccacc caagagc                                              27

<210> SEQ ID NO 45
<211> LENGTH: 27
<212> TYPE: DNA

```
<213> ORGANISM: Artificial Sequence
<220> FEATURE:
<223> OTHER INFORMATION: Synthetic: forward primer for PCR Tm2 V113R

<400> SEQUENCE: 45
gaatccacac ttcgtgggaa tgattcg                                        27

<210> SEQ ID NO 46
<211> LENGTH: 27
<212> TYPE: DNA
<213> ORGANISM: Artificial Sequence
<220> FEATURE:
<223> OTHER INFORMATION: Synthetic: reverse primer for PCR Tm2 V113R

<400> SEQUENCE: 46
cgaatcattc cctcgaagtg tggattc                                        27

<210> SEQ ID NO 47
<211> LENGTH: 27
<212> TYPE: DNA
<213> ORGANISM: Artificial Sequence
<220> FEATURE:
<223> OTHER INFORMATION: Synthetic: forward primer for PCR Tm2 L97T

<400> SEQUENCE: 47
cttactcagt ggaccttgtc atcgagc                                        27

<210> SEQ ID NO 48
<211> LENGTH: 27
<212> TYPE: DNA
<213> ORGANISM: Artificial Sequence
<220> FEATURE:
<223> OTHER INFORMATION: Synthetic: reverse primer for PCR Tm2 L97T

<400> SEQUENCE: 48
gctcgatgac aaggtccact gagtaag                                        27

<210> SEQ ID NO 49
<211> LENGTH: 27
<212> TYPE: DNA
<213> ORGANISM: Artificial Sequence
<220> FEATURE:
<223> OTHER INFORMATION: Synthetic: forward primer for PCR Tm2 W69K

<400> SEQUENCE: 49
tgggcggtat ccaaagagaa cagtaaa                                        27

<210> SEQ ID NO 50
<211> LENGTH: 27
<212> TYPE: DNA
<213> ORGANISM: Artificial Sequence
<220> FEATURE:
<223> OTHER INFORMATION: Synthetic: reverse primer for PCR Tm2 W69K

<400> SEQUENCE: 50
tttactgttc tctttggata ccgccca                                        27

<210> SEQ ID NO 51
<211> LENGTH: 27
<212> TYPE: DNA
<213> ORGANISM: Artificial Sequence
<220> FEATURE:
<223> OTHER INFORMATION: Synthetic: forward primer for PCR Tm2 W80K

<400> SEQUENCE: 51
tccgctacga caaaaagcgg acagttc                                        27
```

```
<210> SEQ ID NO 52
<211> LENGTH: 27
<212> TYPE: DNA
<213> ORGANISM: Artificial Sequence
<220> FEATURE:
<223> OTHER INFORMATION: Synthetic: reverse primer for PCR Tm2 W80K

<400> SEQUENCE: 52
gaactgtccg ctttttgtcg tagcgga                                      27

<210> SEQ ID NO 53
<211> LENGTH: 27
<212> TYPE: DNA
<213> ORGANISM: Artificial Sequence
<220> FEATURE:
<223> OTHER INFORMATION: Synthetic: forward primer for PCR Tm2 N14A

<400> SEQUENCE: 53
ggaacctggt acgcggaact caactcc                                      27

<210> SEQ ID NO 54
<211> LENGTH: 27
<212> TYPE: DNA
<213> ORGANISM: Artificial Sequence
<220> FEATURE:
<223> OTHER INFORMATION: Synthetic: reverse primer for PCR Tm2 N14A

<400> SEQUENCE: 54
ggagttgagt tccgcgtacc aggttcc                                      27

<210> SEQ ID NO 55
<211> LENGTH: 25
<212> TYPE: DNA
<213> ORGANISM: Artificial Sequence
<220> FEATURE:
<223> OTHER INFORMATION: Synthetic: primer Tm2 5' Pci

<400> SEQUENCE: 55
aaaacatgtc agacgttcaa tcttc                                        25

<210> SEQ ID NO 56
<211> LENGTH: 31
<212> TYPE: DNA
<213> ORGANISM: Artificial Sequence
<220> FEATURE:
<223> OTHER INFORMATION: Synthetic: primer TM2 3' Bam

<400> SEQUENCE: 56 tttttggat ccttacttca acctcggtgc g                                  31
```